United States Patent [19]

Kawaguchi et al.

[11] 4,360,434

[45] Nov. 23, 1982

[54] AMPHOTERIC ION-PERMEABLE COMPOSITE MEMBRANE

[75] Inventors: Takeyuki Kawaguchi; Hiroyoshi Minematsu, both of Iwakuni; Yuzuru Hayashi, Kyoto; Shigeyoshi Hara; Fumio Ueda, both of Iwakuni, all of Japan

[73] Assignee: Teijin Limited, Osaka, Japan

[21] Appl. No.: 225,324

[22] Filed: Jan. 15, 1981

[51] Int. Cl.³ .................... B05D 3/10; B05D 5/00
[52] U.S. Cl. ...................... 210/500.2; 210/638; 428/315.5; 428/316.6; 521/27; 521/28; 521/32
[58] Field of Search ............... 428/304, 315.5, 315.7, 428/316.6; 210/500.2, 638; 521/27, 28, 32

[56] References Cited

U.S. PATENT DOCUMENTS 4,262,041  4/1981  Eguchi et al. .............. 210/500.2
4,277,344  7/1981  Cadotte ..................... 210/500.2

Primary Examiner—William J. Van Balen
Attorney, Agent, or Firm—Wenderoth, Lind & Ponack

[57] ABSTRACT

An amphoteric ion-permeable composite membrane composed of a microporous substrate, and supported on the substrate, a thin amphoteric ion-exchange film formed of an active amino group-containing polymer which has been interfacially crosslinked at least at the surface portion of the thin film, said membrane being produced by forming a thin layer comprising an active amino group-containing polymer containing 1.0 to 23 milliequivalents/g, as amino equivalent, of an active amino group selected from primary and secondary amino groups and 0 to 18 milliequivalents/g, as amino equivalent, of a tertiary amino group and/or an ammonium salt group per molecule with the total amino content thereof being in the range of 2.0 to 23 milliequivalents/g on the microporous substrate and then contacting the thin layer on the substrate interfacially with a polyfunctional aromatic compound containing at least two functional groups selected from carbonyl halide groups, sulfonyl halide groups, carboxylic acid anhydride groups, sulfonic acid anhydride groups and derivative groups of carboxylic acids and sulfonic acids having equivalent reactivity to the aforesaid halide and anhydride groups.

25 Claims, No Drawings

AMPHOTERIC ION-PERMEABLE COMPOSITE MEMBRANE

This invention relates to a novel amphoteric ion-permeable composite membrane, and more specifically, to an amphoteric ion-permeable composite membrane having excellent selective ion-permeability and containing an active amino group-containing polymer as a base.

The importance of separation techniques utilizing membranes has increased in recent years because they are energy-saving, resource-saving and pollution-free, which are the favorable aspects required of future technology. Particularly, reverse osmosis membranes and ion exchange membranes are expected to make a marked advance because of their wide applicability.

The reverse osmosis membranes began to find practical applicability when a method was discovered which affords an asymmetric membrane composed of a relatively dense surface skin layer and a coarse porous layer by a phase-separating technique using a cellulose derivative such as cellulose acetate. Since then investigations have been actively undertaken for providing asymmetric membranes from various polymers by a similar method.

This method is an excellent means for meeting the inconsistent requirements of minimizing the thickness of a functional portion which exhibits the performance of a reverse osmosis membrane and of imparting sufficient strength to the membrane against high operating pressures. It has been found, however, that because the dense layer and the porous layer of the membrane obtained by the above method are composed of the same polymer, it cannot have high levels of pressure compaction resistance and chemical resistance.

As an expedient for eliminating such a limitation, a method for producing a composite membrane was proposed which comprises preparing an asymmetrical microporous support membrane from a suitable material, and forming an ultrathin crosslinked membrane on its surface by utilizing interfacial crosslinking reaction in situ. This method opened up a way for supplying excellent reverse osmosis membrane free from the aforesaid limitation.

On the other hand, the ion exchange membranes have been used almost exclusively in an electrodialysis process by which a force is directly exerted on an ion by a difference in electric potential thereby causing ion migration, or as diaphragms in an electrolytic reaction cell, and therefore, the reduction of the membrane thickness as in reverse osmosis membranes has not been so significant a problem. Hence, the ion exchange membranes have been used as fairly thick homogeneous membranes. In theory, however, ion exchange membranes have other applications by utilizing their feature of having a fixed electric charge therein. For example, they may be used in diffusion dialysis which uses a difference in pressure as a driving force and utilizes a difference in ion permeation velocity, Donnan dialysis utilizing the Donnan equilibrium, and pressure dialysis for selective permeation of salts by an amphoteric membrane utilizing a difference in pressure as a driving force. Because of their large thickness, the conventional ion exchange membranes have proved to be inefficient in these theoretical applications and have not gained commercial acceptance.

In view of the above state of the art, the present inventors hit upon an idea of utilizing the aforesaid method for producing a permselective composite membrane for reverse osmosis in producing an ion exchange membrane having a very small effective thickness. Further investigations have led to the present invention.

According to this invention, there is provided an amphoteric ion-permeable composite membrane composed of a microporous substrate, and supported on the substrate, a thin amphoteric ion-exchange film formed of an active amino group-containing polymer which has been interfacially crosslinked at least at the surface portion of the thin film, said membrane being produced by forming a thin layer comprising an active amino group-containing polymer containing 1.0 to 23 milliequivalents/g, as amino equivalent, of an active amino group selected from primary and secondary amino groups and 0 to 18 milliequivalents/g, as amino equivalent, of a tertiary amino group and/or an ammonium salt group per molecule with the total amino content thereof being in the range of 2.0 to 23 milliequivalents/g on the microporous substrate and then contacting the thin layer on the substrate interfacially with a polyfunctional aromatic compound containing at least two functional groups selected from carbonyl halide groups, sulfonyl halide groups, carboxylic acid anhydride groups, sulfonic acid anhydride groups and derivative groups of carboxylic acids and sulfonic acids having equivalent reactivity to the aforesaid halide and anhydride groups; the interfacially crosslinked polymer zone of the thin film containing at least one structural unit of the formula

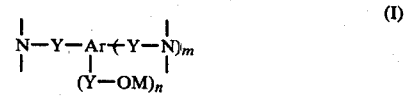

wherein Ar represents an aromatic ring, Y represents CO or $SO_2$ provided that $(m+n+1)$ group Y bonded to the group Ar are identical or different, M represents an atom or atomic grouping capable of being split off as a cation, and m and n each represent an integer of 0 or more provided that $m+n=1-3$, said polymer zone further containing a structural unit of formula (I) in which m is not zero when it contains a structural unit of formula (I) in which m is zero, and further containing a structural unit of formula (I) in which n is not zero when it contains a structural unit of formula (I) in which n is zero, and additionally containing at least 0.5 milliequivalent/g, based on the crosslinked polymer (dry), of an ammonium salt group as a cation-exchange group and at least 0.05 milliequivalent/g of the crosslinked polymer (dry) of the group -YOM in formula (I) as an anion-exchange group, the equivalent ratio of the ammonium salt group to the group -YOM being in the range of from 20:1 to 1:2.

The active amino group-containing polymer used to form the amphoteric ion-permeable layer of the amphoteric ion-permeable composite membrane contains 1.0 to 23 milliequivalents/g of the dry polymer, preferably 2.0 to 20 milliequivalents/g of the dry polymer, more preferably 3.0 to 17 milliequivalents/g of the dry polymer. of an active amino group selected from primary and secondary amino groups in the main chain and/or side chain. Any active amino group-containing polymers containing the active amino groups in such amounts and being frequently used in the product of semipermeable composite membranes in the field of reverse osmosis membranes can be used in the production of the membrane of this invention.

The active amino group-containing polymer used in this invention (to be sometimes referred to hereinbelow as "amino-polymer") may further contain a tertiary amino group and/or an ammonium salt group. The tertiary amino group and/or ammonium salt group may be present in the amino-polymer in an amount of at most 18 milliequivalents, preferably at most 12 milliequivalents, more preferably 1.0 to 9.0 milliequivalents, per gram of the dry polymer.

The amino polymer used in this invention may contain the active amino groups selected from primary and secondary amino groups and the tertiary amino group and/or ammonium salt group in a total amount of 2.0 to 23 milliequivalents/g of the dry polymer. The preferred total amino content is 3.0 to 23 milliequivalents/g of the dry polymer, and the more preferred total amino content is 4.0 to 23 milliequivalents/g of the dry polymer.

In the present specification and the appended claims, the term "total amino content" denotes the content of all amino groups including not only primary, secondary and tertiary amino groups but also the ammonium salt group. It should be understood therefore that unless otherwise specified, the expression "amino group" used herein is meant to include not only primary, secondary and tertiary amino groups but also the ammonium salt group.

Amino-polymers which can be advantageously used in this invention contain 1.0 to 23 milliequivalents/g as amino equivalent, of active amino groups selected from primary and secondary amino groups and 0 to 18 milliequivalents/g as amino equivalent of tertiary amino groups and/or ammonium salt groups with the total amino content thereof being in the range of 2.0 to 23 milliequivalents/g.

Examples of the tertiary amino groups and ammonium salt groups which may optionally be present in the amino-polymer used in this invention are shown below.

(i) Tertiary amino groups

Desirably, the tertiary amino groups are those which can be easily converted to ammonium salt groups in situ by reaction with hydrogen halides released by the interfacial crosslinking reaction to be described hereinbelow. Examples of such tertiary amino groups are given below.

wherein $R_1$ and $R_2$ represents a hydrocarbon group containing not more than 10 carbon atoms which may contain a heteroatom such as a nitrogen, oxygen or sulfur atom, a direct bond, or a hydrogen atom; $R_3$ represents a hydrocarbon group having not more than 10 carbon atoms which may have a heteroatom such as a nitrogen, oxygen, sulfur or halogen atom; $R_3$ may form the main polymer chain, or may bond

present in the terminal of the side chain to the main chain; when $R_1$ or $R_2$ represents a direct bond, it may bond $R_3$ to N to form a heteroaromatic ring such as a pyridine ring or quinoline ring; either one of $R_1$ and $R_2$ may be bonded to $R_3$ to form a ring, or both of these may be bonded to form a ring; and $R_1$ and $R_2$ are not necessarily monovalent groups, and may be bonded to other groups which are different from any of $R_1$, $R_2$ and $R_3$.

Among these tertiary amino groups, those of the following formulae (II-a) to (II-d) are preferred.

Acyclic tertiary amino groups of the formula

wherein $R_4$ and $R_5$ represent a hydrogen atom or a hydrocarbon group having 1 to 4 carbon atoms which may contain a nitrogen atom; $R_6$ is as defined with respect to $R_3$; and $R_5$ may be bonded to another group to form a bonded chain.

Piperazine-type tertiary amino groups of the formula

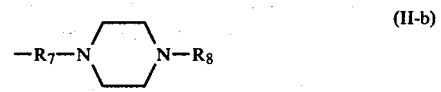

wherein $R_7$ represents a hydrocarbon group having not more than 10 carbon atoms, and $R_8$ represents a hydrogen atom or a hydrocarbon group having 1 to 4 carbon atoms.

Piperidine-type tertiary amino groups of the formula

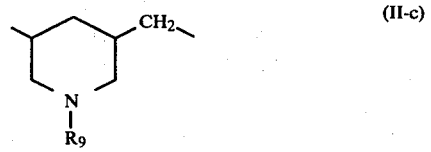

wherein $R_9$ represents a hydrogen atom, an alkyl group having 1 to 4 carbon atoms, a phenyl group or a cycloalkyl group having not more than 10 carbon atoms.

A pyridine-type tertiary amino group of the formula

(ii) Ammonium salt groups

These ammonium salt groups are represented by the following formula

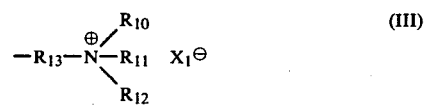

wherein $R_{10}$, $R_{11}$ and $R_{12}$ represent a hydrogen atom, a direct bond, or a hydrocarbon group having not more than 10 carbon atoms which may have a heteroatom such as a nitrogen, oxygen or sulfur atom; $R_{13}$ represent a hydrocarbon group having not more than 10 carbon atoms which may contain a heteroatom such as a nitrogen, oxygen, sulfur or halogen atom, which may constitute the main chain or may bond

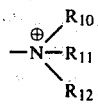

present in the terminal of the side chain to the main chain; $X^\ominus$ represents an organic or inorganic anion; when $R_{10}$, $R_{11}$ or $R_{12}$ represent a direct bond, it may bond $R_{13}$ to $N^\oplus$ to form a heteroaromatic ring such as a pyridine or quinoline ring; any one of $R_{10}$, $R_{11}$ and $R_{12}$ may be bonded to $R_{13}$ to form a ring, or two of them may be bonded to each other to form a ring; and $R_{10}$, $R_{11}$ and $R_{12}$ are not necessarily monovalent groups, and may be bonded to other groups different from any of these.

Among the above ammonia salt groups, those of the formulae (III-a) to (III-e) are preferred.

Acyclic ammonium salt groups of the formula

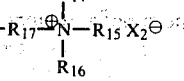 (III-a)

wherein $R_{14}$, $R_{15}$ and $R_{16}$ represent a hydrogen atom or a hydrocarbon group having 1 to 4 carbon atoms which may contain a nitrogen atom; $X_2^\ominus$ represents an inorganic anion or an organic anion having not more than 2 carbon atoms; and $R_{15}$ and/or $R_{16}$ may be bonded to another group to form a bonded chain.

Piperazine-type ammonium salt groups of the following formulae

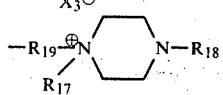 (III-b)

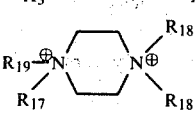 (III-c)

wherein $R_{17}$ represents a hydrogen atom or a hydrocarbon group having not more than 10 carbon atoms; $R_{19}$ represents a hydrocarbon group having not more than 10 carbon atoms; $R_{18}$ represents a hydrogen atom or a hydrocarbon group having not more than 10 carbon atoms; and $X_3^\ominus$ is the same as $X_2^\ominus$.

Piperidine-type ammonium salt groups of the formula

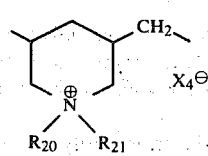 (III-d)

wherein $R_{20}$ and $R_{21}$, independently from each other, represent a hydrogen atom, an alkyl group having 1 to 4 carbon atoms, a phenyl group, or a cycloalkyl group having not more than 10 carbon atoms, or may be bonded to each other to form a ring together with the nitrogen atom to which they are bonded; and $X_4^\ominus$ is the same as $X_2^\ominus$.

Pyridine-type ammonium salt groups of the following formula

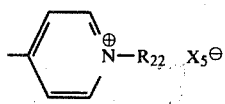 (III-e)

wherein $R_{22}$ represents a hydrogen atom or a hydrocarbon group having not more than 10 carbon atoms, and $X_5^\ominus$ is the same as $X_2^\ominus$.

The amino polymer should form a continuous thin layer on the microporous substrate, and desirably has a number average molecular weight of generally 500 to 200,000, preferably 700 to 150,000. Advantageously, the amino-polymer has an intrinsic viscosity $[\eta]$, measured at 30° C. in a 1/10 N aqueous NaCl solution, of generally 0.05 to 5.0 dl/g, preferably 0.07 to 3.0 dl/g, more preferably 0.1 to 2.0 dl/g.

In forming a thin layer of the amino-polymer on the microporous substrate, the amino-polymer is applied in solution form to the microporous substrate as is done conventionally. Accordingly, the amino-polymer should be soluble in a solvent. For convenience of operation, the solvent is desirably water, or a water-miscible organic solvent having a boiling point of not more than 140° C., preferably not more than 120° C., or a mixture of at least two of these. It is advantageous that the amino-polymer used in this invention has a solubility at 20° C. of generally not less than 0.2% by weight, preferably not less than 0.5% by weight, more preferably not less than 1.0% by weight, in at least one solvent selected from the group consisting of water and water-miscible organic solvents having a boiling point of not more than 140° C., preferably not more than 120° C.

Examples of the water-miscible organic solvents include methanol, ethanol, propanol, tetrahydrofuran, acetone, methyl ethyl ketone, methyl isobutyl ketone, diethyl ether, and dioxane.

The amino-polymer at least contains structural units composed of a primary and/or a secondary amino group and a hydrocarbon group having 2 to 20 carbon atoms, preferably 2 to 15 carbon atoms, which may contain in addition to the active amino group, a nitrogen atom (N), an oxygen atom (O), a halogen atom (e.g., chlorine or bromine), or a sulfur atom (S) as a heteroatom. When there is a hetero atom, it may exist in various forms. For example, the nitrogen atom may exist in the form of a tertiary amino group or an ammonium salt group; the oxygen atom may exist in the form of an ether linkage, an ester linkage, a carbonyl linkage or a hydroxyl group; and the halogen atom may exist as a substituent for hydrogen.

Examples of preferred structural units are those of the following general formula (IV), (V), (VI), and (VII).

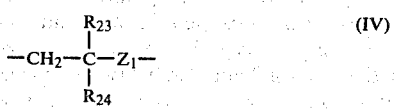 (IV)

wherein $Z_1$ represents a direct bond, —O—,

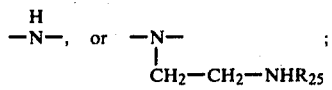

$R_{23}$ represents a hydrogen atom or a methyl group; when $Z_1$ is

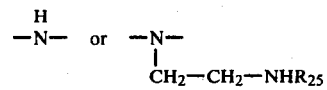

$R_{24}$ represents a hydrogen atom, and when $Z_1$ represents a direct bond or —O—, $R_{24}$ represents the group —$Z_2$—$R_{26}$; $R_{25}$ represents an alkyl group having 1 to 5 carbon atoms; $Z_2$ represents a direct bond, —O—,

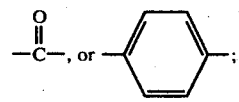

$R_{26}$ represents the group —$NHR_{27}$, —$R_{28}$—$NHR_{29}$; $R_{27}$ and $R_{29}$ represent an alkyl group having 1 to 5 carbon atoms; and $R_{28}$ represents a divalent aliphatic group (e.g., alkylene group) having 1 to 5 carbon atoms which may contain an oxygen atom.

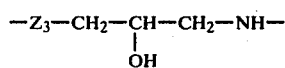     (V)

wherein $Z_3$ represents a direct bond or —O—.

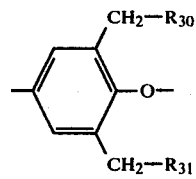     (VI)

wherein $R_{30}$ represents a halogen atom or the group —$NHR_{32}$; $R_{31}$ represents the group —$NHR_{32}$; and $R_{32}$ represents a hydrogen atom or an alkyl group having 1 to 5 carbon atoms.

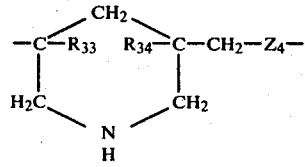     (VII)

wherein $R_{33}$ and $R_{34}$, independently from each other, represent a hydrogen atom or a methyl group, and $Z_4$ represents a direct bond or —$SO_2$—.

The amino polymer used in this invention may include those which gel by itself upon heating or those which have no self-gelling ability. When the process of this invention is carried out using an amino polymer of the self-gelling type having too low a gelling temperature, its self-gellation is likely to proceed substantially before the reaction of the active amino group in the polymer with the polyfunctional compound is substantially completed. It is very desirable therefore that the amino polymer used in this invention, even if when it is of the self-gelling type, should not gel at a temperature below 50° C., preferably below 60° C.

Specific examples of the amino polymer are given below. It is to be understood that these examples are merely illustrative for facilitating an understanding of the invention, and do not in any way limit the scope of this invention.

(I) Amino polymers which have only primary amino groups in the polymer molecule as amino groups having an active hydrogen atom (active amino groups) and do not gel by itself at a temperature of 120° C. or below:

Typical examples of the amino polymer which belongs to this group are as follows:

(a) Polyvinyl amine type polymers which are homopolymers or copolymers having structural units of the formula

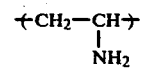

(b) Polyaminostyrene-type polymers which are homopolymers or copolymers having structural units of the formula

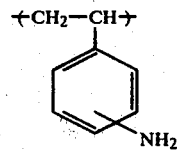

(c) Polyallylamine-type polymers which are homopolymers or copolymers having structural units of the formula

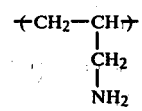

(d) Homopolymers or copolymers having structural units of the formula

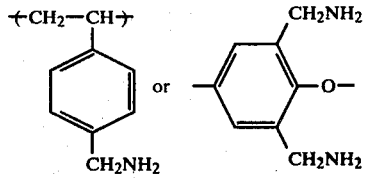

(see, for example, European Patent Publication No. 10,425).

(II) Amino polymers which contain only primary amino groups as the active amino groups in the polymer molecule and have self-gelling ability at an elevated temperature:

Typical examples of the amino polymer of this group are as follows:

(a) Partially ammonia-modified polyepichlorohydrin which is a polymer consisting mainly of structural units of the formula

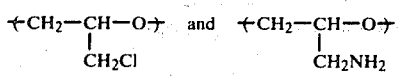

for example, the polymer described in U.S. Pat. No. 4,005,012.

(b) Partially ammonia-modified poly(chloroethyl vinyl ether) which is a polymer consisting mainly of structural units of the formulae

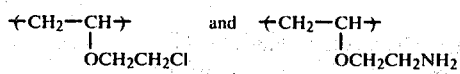

(for example, the polymer described in European Patent Publication No. 10,425).

(c) Partially hydrazine-modified poly[(meth)acrylate] which is a polymer consisting mainly of structural units of the formulae

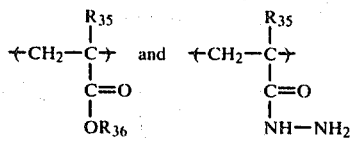

wherein $R_{35}$ represents a hydrogen atom or a methyl group, all $R_{35}$ groups may not always be the same, and $R_{36}$ represents an alkyl group having 1 to 4 carbon atoms, for example the polymer described in European Patent Publication No. 8,945.

(d) Ammonia-modified poly[glycidyl (meth)acrylate] which is a polymer consisting mainly of structural units of the formula

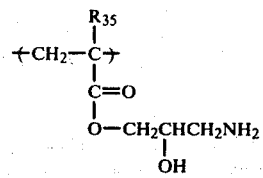

wherein $R_{35}$ is the same as defined hereinabove, for example the polymer described in European Patent Publication No. 10,425.

(III) Amino polymers which have both a primary amino group and a secondary amino group in the polymer molecules and do not have self-gelling property at an elevated temperature:

Typical amino polymers of this group are the polyaddition products between polyepoxy compounds and polyamino compounds having at least two active amino groups which are disclosed in DAS No. 2822784. More specific examples are polymers consisting mainly of the following structural units.

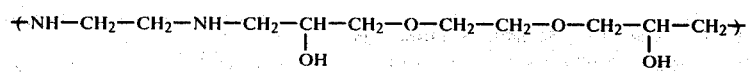 (a)

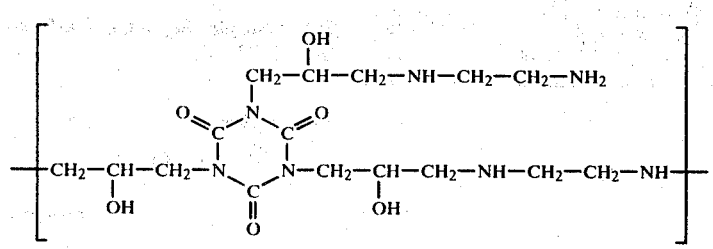 (b)

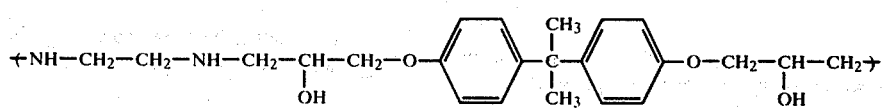 (c)

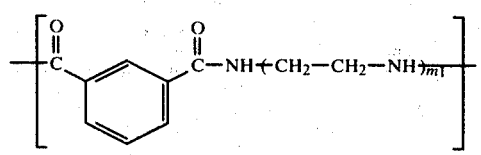

($m_1 \geq 1$)

(e) Polyethylenimine consisting mainly of structural units of the formula

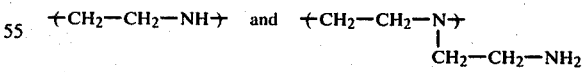

particularly the one described in U.S. Pat. No. 4,039,440.

(IV) Amino-polymers containing a primary amino group and a secondary amino group as the active amino groups in the polymer molecule and having self-gelling ability at an elevated temperature:

Examples of the amino-polymers of this group are as follows:

(a) Polyamine-modified polyepichlorohydrin, for example a polymer consisting mainly of structural units of the formula

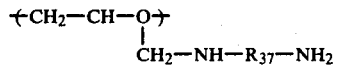

wherein R₃₇ represents an aliphatic hydrocarbon radical containing 2 to about 15 carbon atoms which may contain a nitrogen atom in the form of a primary, secondary or tertiary amino group and an oxygen atom in the form of a hydroxyl group or ether bond, an alicyclic hydrocarbon containing from about 4 to about 8 carbon toms in the ring, or a heterocyclic radical, which is described in U.S. Pat. No. 4,005,012.

(b) Polyamine-modified poly(2-chloroethylvinyl ether), for example a polymer consisting mainly of structural units of the formula

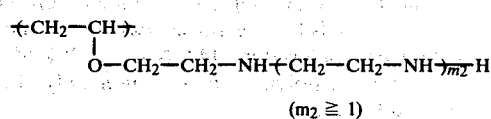

$(m_2 \geq 1)$ especially the one described in European Patent Publication No. 10,425.

(V) Amino polymers which have only secondary amino groups as the active amino groups and do not have self-gelling ability at an elevated temperature:

The amino polymers of this group include polymers consisting of structural units of formula (VII) given hereinabove particularly structural units of the formula

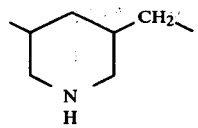

and polymers consisting mainly of at least one structural units selected from the following group:

 (a)

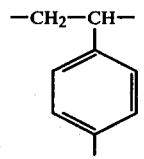 (b)

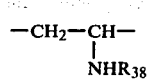 (c)

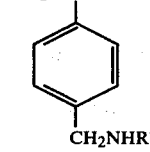 (d)

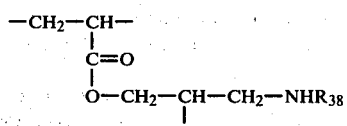 (e)

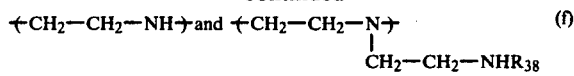 (f)

(for example, see U.S. Pat. No. 3,951,815)

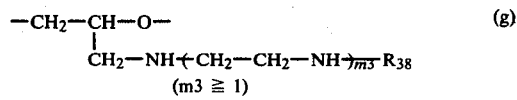 (g)

$(m_3 \geq 1)$ (for example, see U.S. Pat. No. 4,005,012) wherein R₃₈ represents an alkyl group having 1 to 5 carbon atoms.

(VI) Polymers which have only secondary amino groups as the active amino groups in the polymer molecules and have self-gelling ability at an elevated temperature:

The amino polymers of this group include polymers consisting mainly of structural units selected from the following group:

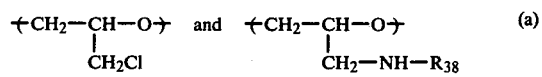 (a)

(for example, Japanese Laid-Open Patent Publication No. 67573/79)

 (b)

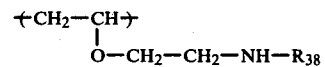

(for example, U.S. patent application Ser. No. 86192 filed Nov. 15, 1979)

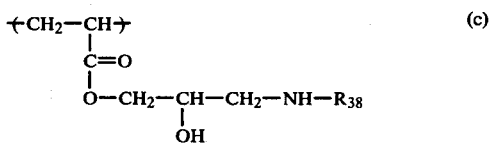 (c)

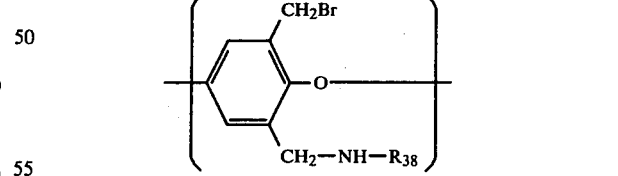 (d)

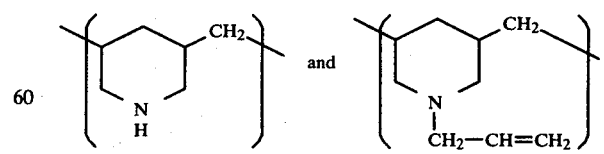

In the above formulae, R₃₈ is as defined hereinabove.

It should be understood that the disclosures of the patent specification cited herein in the exemplification of the amino polymer form part of the specification of the present application.

Among the above amino polymers, those which can be preferably used in this invention are the polymers (A) to (D) below.

(A) The addition polymer between a polyepoxy compound and a polyamine compound having at least two active amino groups which is described, for example, in DAS No. 2822784.

(B) Polyethylenimine, polyamine-modified polyepichlorohydrin and polyamine-modified poly(2-chloroethylvinyl ether) (see U.S. Pat. Nos. 4,039,440 and 4,005,012 and European Patent Publication No. 10,425).

(C) Polymers containing at least 30 mole% of structural units of the following formula

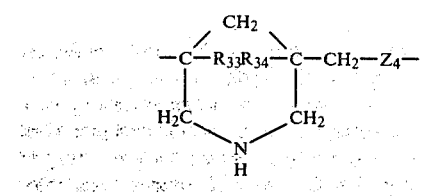

wherein $R_{33}$, $R_{34}$ and $Z_4$ are as defined hereinabove (see U.K. Patent Application No. 2027614).

(D) Polymers consisting mainly of two structural units of the formulae

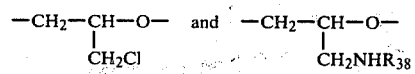

or of two structural units of the formulae

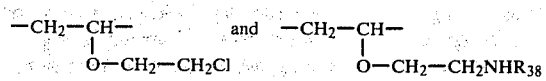

wherein $R_{38}$ is as defined above (see Japanese Patent Publication No. 67573/79 and European Patent Publication No. 10,425).

Amino-polymers containing a tertiary amino group and/or an ammonium salt group may, for example, be those resulting from conversion of a part of the active groups of amino polymers into a tertiary amino group or an ammonium salt group. Typical examples of such amino polymers having an ammonium salt group are as follows:

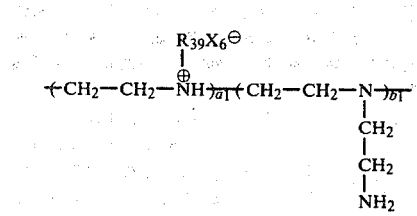

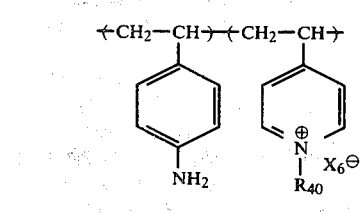

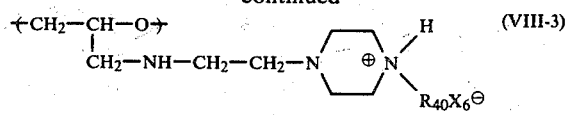

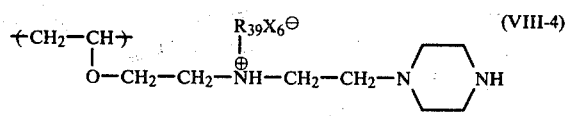

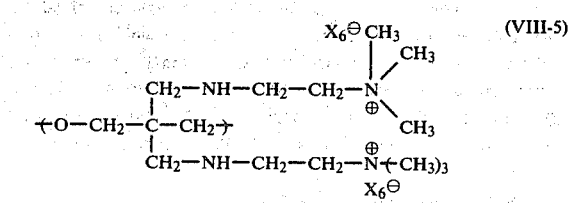

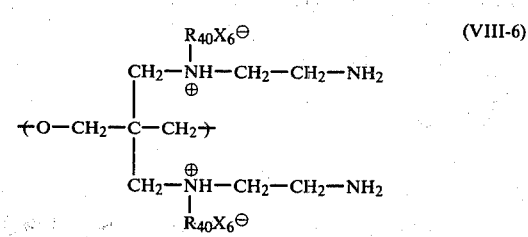

In the above formulae, $a_1$ and $b_1$ represent copolymerization ratios, and are not particularly critical. They are selected so as to meet conditions relating to the equivalent ratio of amino groups in the amino polymers. $R_{39}$ represents a hydrogen atom or a hydrocarbon group having 1 to 4 carbon atoms which may contain a nitrogen atom, $R_{40}$ represents a hydrogen atom or a hydrocarbon group having not more than 10 carbon atoms, and $X_6^\ominus$ represents a halogen ion.

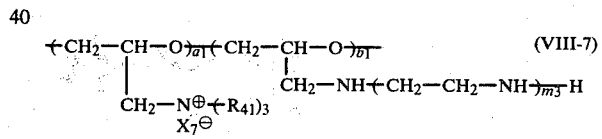

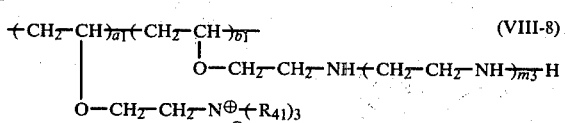

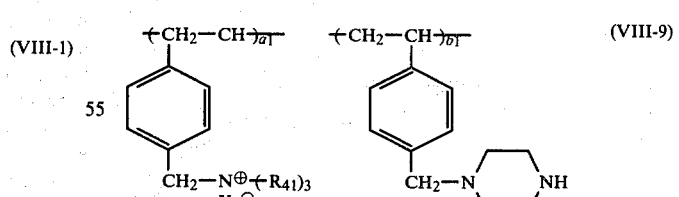

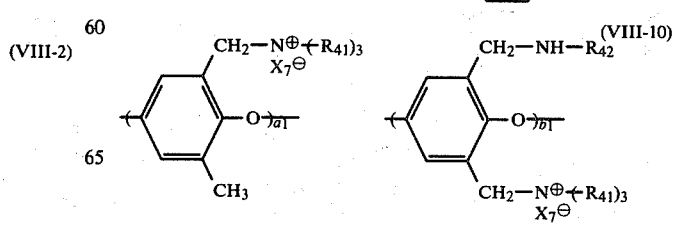

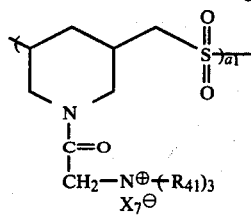 (VIII-11) 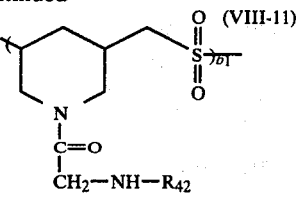 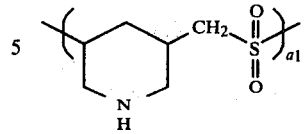

In the above formulae, $R_{41}$ and $R_{42}$, independently from each other, represent a hydrogen atom, an alkyl group having 1 to 4 carbon atoms, a phenyl group or a cycloalkyl group having 5 to 10 carbon atoms; $X_7^-$ represents a halogen atom; $m_3$ represents 0 or an integer of 1 to 10; and $a_1$ and $b_1$ are as defined hereinabove.

(VIII-12) Polydiallylamine-type copolymers

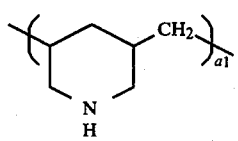 (i)

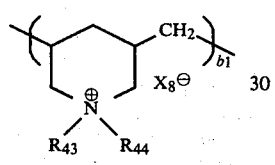 (ii)

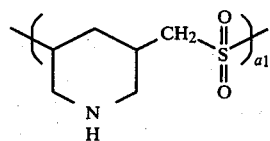

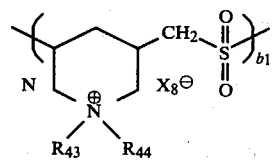 (iii)

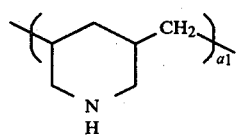

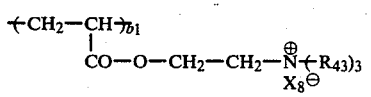

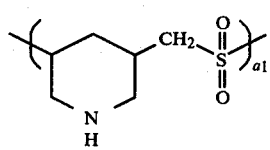 (iv)

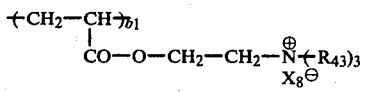

(VIII-12) Polydiallylamine-type copolymers

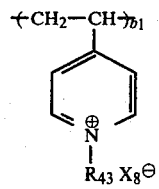 (v)

In the above formulae, $R_{43}$ and $R_{44}$, independently from each other, represent a hydrogen atom, an alkyl group having 1 to 4 carbon atoms, a phenyl group or a cycloalkyl group having 5 to 10 carbon atoms provided that two or more $R_{43}$ groups bonded to the nitrogen atom may be identical or different; $X_8$ represents a halogen atom, $-HSO_4$, $-NO_3$, $CH_3COO-$, or $HCOO$; and $a_1$ and $b_1$ are as defined hereinabove.

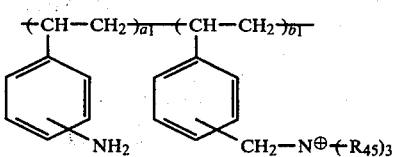 (VIII-13)

wherein $R_{45}$ represents a hydrogen atom or an alkyl group having 1 to 3 carbon atoms provided that two or more $R_{45}$ groups may be identical or different; $X_9$ represents a halogen atom; and $a_1$ and $b_1$ are as defined hereinabove.

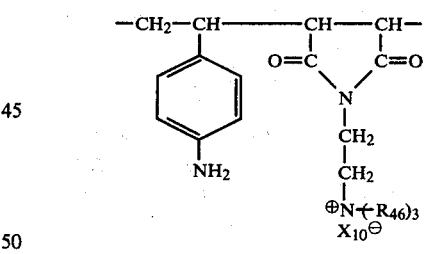 (VIII-14)

wherein $R_{46}$ represents a hydrogen atom or an alkyl group having 1 to 3 carbon atoms provided that two or more $R_{46}$ groups may be identical or different, and $X_{10}$ represents a halogen atom.

The aforesaid amino polymer at least containing a primary and/or a secondary amino group and the amino polymer containing an ammonium salt group may be used as a mixture. Or polymers of the type in which the structural units of these polymers are exchanged with each other may be produced and used for the purpose of this invention.

Among the above-mentioned starting amino polymers, aliphatic active amino group-containing polymers are preferred. Desirably, the amino groups present in these polymers should not be spaced from each other too far. Especially preferred are those in which the number of carbon atoms which constitute the chain connecting two adjacent amino groups (including the ammonium salt groups as stated hereinabove) in the same molecule is generally 2 to 10, preferably 2 to 8, more preferably 2 to 6.

Suitable amino-polymers are those which gel by itself upon heating. By using these polymers, an internal anchor layer which is water-insoluble and has markedly improved properties such as oxidation resistance, soiling resistance and pressure compaction resistance (or mechanical strength) can be formed by heat-treatment between the microporous substrate and the interfacially crosslinked polymer zone in the surface of the thin film of the composite membrane formed after the interfacial crosslinking reaction to be described hereinbelow.

It is possible to incorporate into the amino polymer a compound (to be referred to hereinbelow as an "internal crosslinking agent") having per molecule at least two functional groups ($F_1$) which do not substantially react with the primary or secondary amino groups in the polymer at the temperature at which the interfacial crosslinking to be described is carried out, but can easily react with either one or the primary or secondary amino group in the polymer at a temperature at least 30° C. higher than the above crosslinking temperature. As a result, heat crosslinkability can be imparted to the amino polymer having no self-gelling property, or the amino polymer having self-gelling ability can be crosslinked at lower heating temperatures. This leads to the production of an amphoteric ion-permeable composite membrane having greatly improved durability and water resistance.

Accordingly, the thin film formed in accordance with the present invention desirably contains such an internal crosslinking agent in addition to the amino polymer.

The expression "the functional groups $F_1$ do not substantially react", as used herein, means that at a temperature in question, such as the temperature at which the interfacial crosslinking is carried out, the functional groups $F_1$ do not at all react with the polymer, or react with it to an extent of at most 10 mole %, preferably at most 5 mole %, of the functional groups $F_1$.

Likewise, the expression "the functional groups $F_1$ can easily react", means that at the temperature in question, the functional groups react with the polymer to an extent of at least 30 mole %, preferably at least 50 mole %.

The functional groups $F_1$ can be selected from a wide range of groups so long as they meet the aforesaid limitations. Advantageously, they are functional groups which do not substantially react with any of the primary and secondary amino groups in the polymer at a temperature of not more than 20° C., preferably not more than 30° C., but can easily react with either the primary or secondary amino groups or both in the polymer at a temperature of at least 50° C., preferably at least 70° C. but lower than the self-gelling temperature (T°C.) of the amino polymer, preferably not more than (T-20)°C.

The self-gelling temperature, as used herein, denotes a temperature at which 70% by weight of a polyamino polymer becomes water-soluble when a solution of the amino polymer alone in the same concentration as the amino polymer in the thin layer to be subjected to interfacial crosslinking reaction is maintained for 30 minutes.

The type of the functional groups ($F_1$) meeting this requirement differs depending upon the types of the primary and/or secondary amino groups in the amino polymer, the mode of bonding thereof in the polymer structure, etc., but generally they can be selected from the following group.

—CH(OH)CH$_2$X$_{11}$,
—COOA$_1$,
—NHCOOA$_2$,

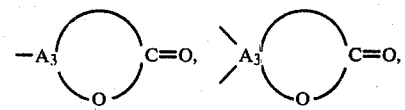

—COCH=CH$_2$,

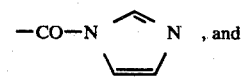

and active halomethyl groups.

In the above formulae, $X_{11}$ represents a halogen atom, $A_1$ and $A_2$ each represent a hydrogen atom or an organic radical capable of being split off together with the oxygen atom to which it is bonded, and $A_3$ represents a trivalent or tetravalent saturated aliphatic group having 2 to 5 carbon atoms.

The "halogen atom" represented by $X_{11}$ denotes four elements, fluorine, chlorine, bromine and iodine, the chlorine atom being preferred. Examples of the "organic radical capable of being split off together with the oxygen atom to which it is bonded" represented by $A_1$ and $A_2$ are —CH$_3$, —C$_2$H$_5$, —C$_3$H$_7$, —C$_4$H$_9$, —CH$_2$CH=CH$_2$, —CH$_2$—C$_6$H$_5$ and —C$_6$H$_5$. Specific examples of the "trivalent or tetravalent saturated aliphatic group having 2 to 5 carbon atoms" are

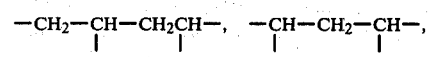

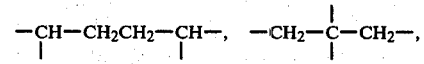

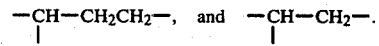

The term "active halomethyl group" denotes the group —CH$_2$X$_{12}$ bonded to a carbonyl group, a benzyl group, an allyl group, etc., in which $X_{12}$ is a halogen atom, preferably Cl and Br.

Typical examples of the functional groups ($F_1$) are given below.

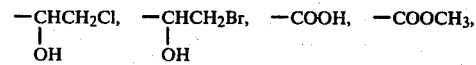

—COOC$_2$H$_5$, —COOC$_3$H$_7$, —COOC$_4$H$_9$,

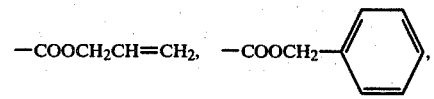

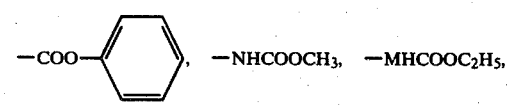

-continued

—NHCOOC$_3$H$_7$, —NHCOOC$_4$H$_9$, —NHCOOCH$_2$CH=CH$_2$,

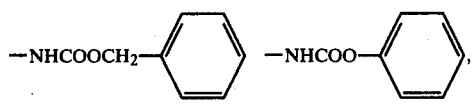

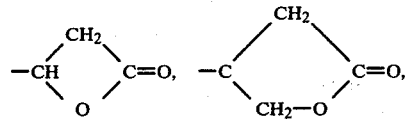

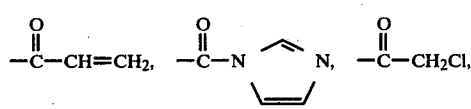

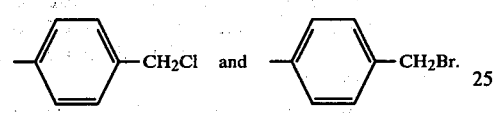

The internal crosslinking agent in this invention has at least two such functional groups (F$_1$) per molecule, and the two or more functional groups (F$_1$) may be identical or different.

Since the internal crosslinking agent is used as a uniform dispersion in the amino polymer, it is very desirable that it be soluble to some extent in a solvent for the polymer, i.e. at least one solvent selected from water and water-miscible organic solvents having a boiling point of not more than 140° C. Generally, it is advantageous that the internal crosslinking agent be soluble at 20° C. in the solvent to an extent of at least 0.1 g/100 ml of solvent, preferably at least 0.2 g/100 ml of solvent, more preferably at least 0.5 g/100 ml of solvent.

The type of the internal crosslinking agent used in this invention is not particularly limited so long as it has at least two functional groups (F$_1$) and shows the above-mentioned solubility. It may be of low to high molecular weight.

Suitable low-molecular-weight internal crosslinking agents are organic compounds, especially aliphatic organic compounds, generally containing 2 to 4, preferably 2 to 3, functional groups (F$_1$) per molecule and having a molecular weight of 90 to 500, preferably 100 to 500. Suitable high-molecular-weight internal crosslinking agents are high-molecular-weight polyfunctional organic compounds, especially vinyl polymers, which contain the functional groups (F$_1$) in an amount of 2.0 to 15.0 milliequivalents, especially 5.0 to 15.0 milliequivalents, per gram of the compounds, and have a number average molecular weight of 1,000 to 100,000, preferably 2,000 to 10,000.

Typical examples of the internal crosslinking agent that can be used in this invention are as follows:

(A) Low-molecular-weight internal crosslinking agents

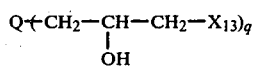 (i)

wherein X$_{13}$ represents a halogen atom, preferably a chlorine atom, Q represents an alkyl group having 2 to 20 carbon atoms which may contain an oxygen atom or a halogen atom, a direct bond or an ether linkage, and q is an integer of 2 to 6.

Specific examples are as follows:

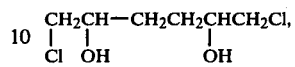

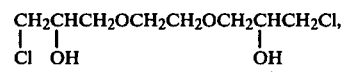

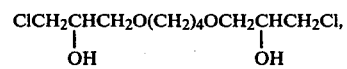

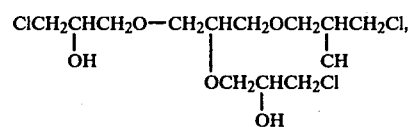

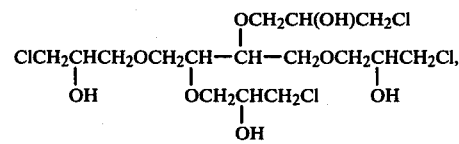

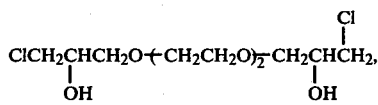

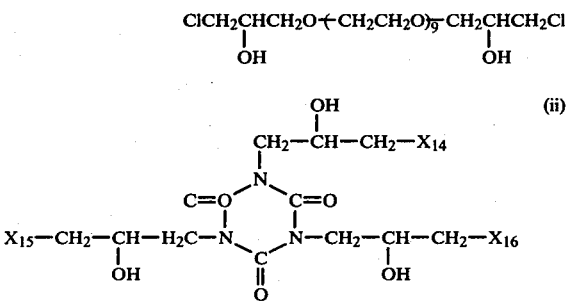

wherein X$_{14}$, X$_{15}$ and X$_{16}$ each represent a halogen atom, preferably a chlorine atom.

(iii) A$_4$—(COOA$_5$)$_a$ wherein A$_4$ represent a hydroxyl group, a sulfonic acid salt group, a carboxylic acid salt group, an aliphatic group containing 1 to 12 carbon atoms and having a valence of a which may contain an oxygen or halogen atom, an aromatic group containing 6 to 10 carbon atoms and having a valence of a, or an alicyclic group containing 5 or 6 to carbon atoms and having a valence of a, A$_5$ represents an alkyl group having 1 to 4 carbon atoms, an allyl group, an aralkyl group having 7 to 10 carbon atoms, or a phenyl group, and a is an integer of 2 to 4.

The "aliphatic group" may be of linear or branched chain, and saturated or unsaturated (containing a double bond), and the "aromatic group" may consist of a benzene ring.

Specific examples of the compounds (iii) are as follows:

HOOC—CH₂—COOH, HOOC—CH₂CH₂—COOH, HOOC—CH₂—CH₂—CH₂—COOH, H₃—COOC—CH₂—COOH,

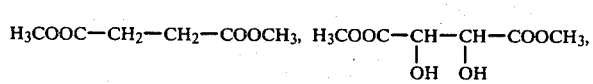
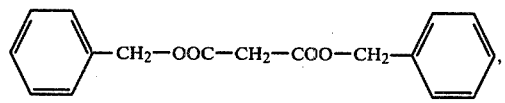

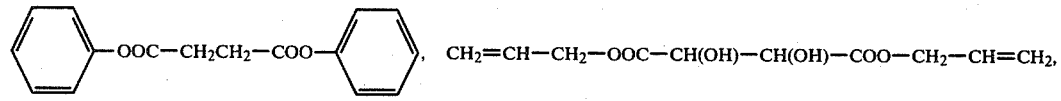

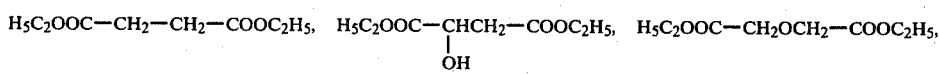

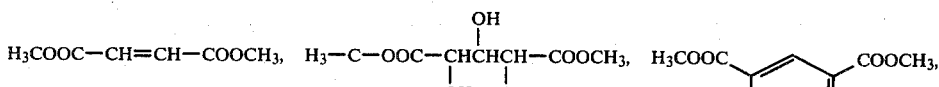
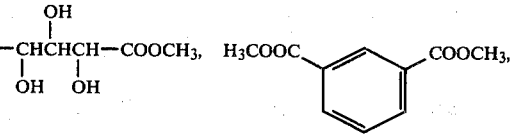

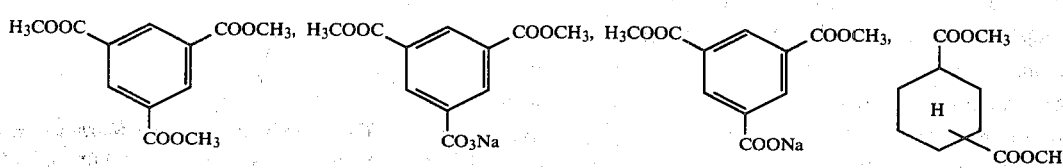

(iv) A₆—OOCNH—A₈—A₇ wherein A₆ and A₇ each represent an alkyl group having 1 to 4 carbon atoms, an allyl group, an aralkyl group having 7 to 10 carbon atoms, or a phenyl group, and A₈ represents an alkylene group having 2 to 10 carbon atoms, or an arylene group which may be substituted by a halogen atom or an alkyl group having 1 to 6 carbon atoms.

Specific examples of the compounds (iv) are given below.

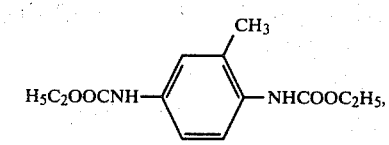

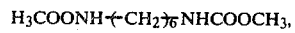

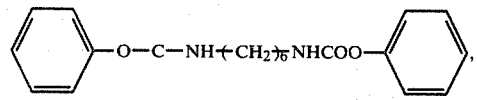

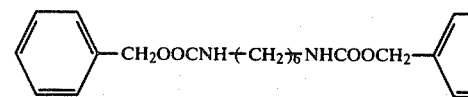

(v) A₉—(OOC—CH=CH₂)_b wherein A₉ represents a hydroxyl group, a sulfonic acid salt group, a carboxylic acid salt group, an aliphatic group containing 1 to 12 carbon atoms and having a valence of b which may contain an oxygen or halogen atom, an aromatic group containing 6 to 10 carbon atoms and having a valence of b, or an alicyclic group containing 5 or 6 carbon atoms and having a valence of b, and b is an integer of 2 to 4.

Specific examples of the compounds (v) include the following.

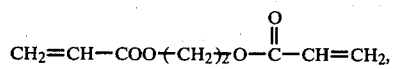

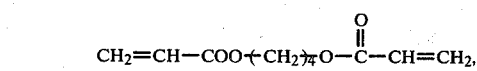

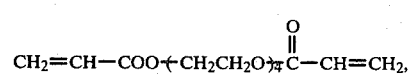

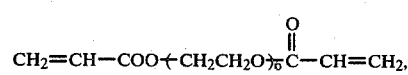

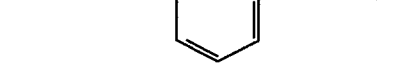

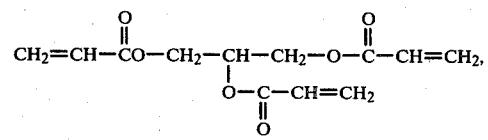

-continued

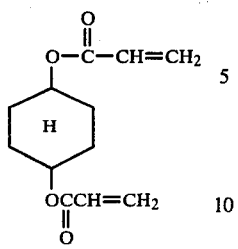

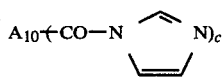     (vi)

wherein $A_{10}$ represents a hydroxyl group, a sulfonic acid salt group, a carboxylic acid salt group, an aliphatic group containing 1 to 12 carbon atoms and having a valence of c which may contain an oxygen or halogen atom, an aromatic group containing 6 to 10 carbon atoms and having a valence of c, or an alicyclic group containing 5 or 6 carbon atoms and having a valence of c, and c is an integer of 2 to 4.

Specific examples of the compounds (vi) are as follows:

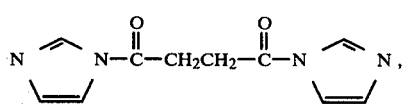

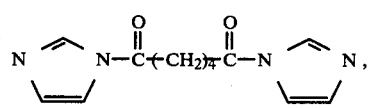

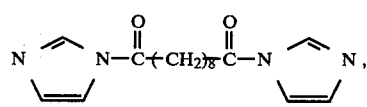

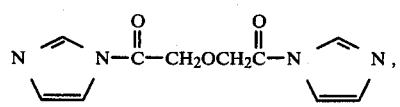

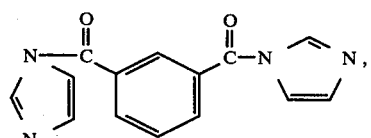

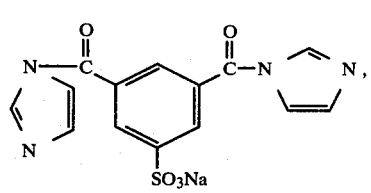

-continued

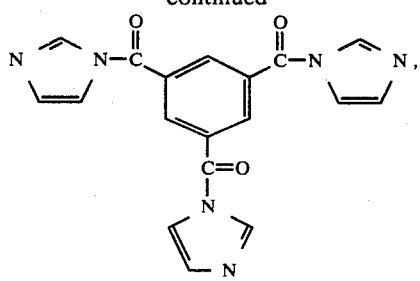

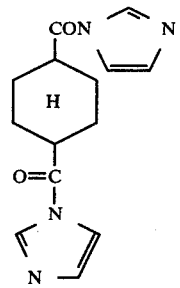

(vii) $X_6$-$CH_2$-COO-$A_{11}$ wherein $X_6$ represents a halogen atom, and $A_{11}$ represents an alkyl group having 1 to 4 carbon atoms, an allyl group, a phenyl group and an aralkyl group having 7 to 10 carbon atoms.

Examples of the compounds (vii) include the following.

$ClCH_2COOH$, $BrCH_2COOH$, $ClCH_2COOCH_3$, $ClCH_2COOC_2H_5$, $ClCH_2COOCH_2CH=CH_2$,

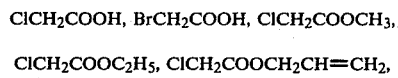

Among the above examples, especially preferred low-molecular-weight internal crosslinking agents (i) to (vii) are shown below.

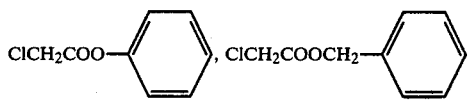     (i)

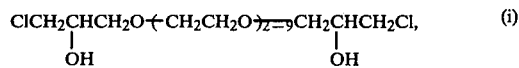     (ii)

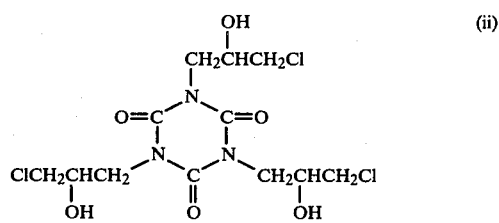     (iii)

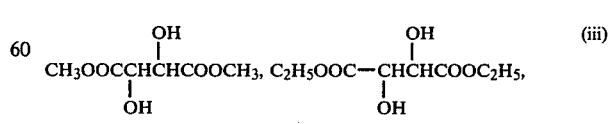

$H_2COOCNH$+$CH_2$+$_6$$NHCOOCH_3$,     (iv)

-continued $$CH_2=CHCH_2OOCNH(CH_2)_6NHC(=O)-CH_2,$$
$$\quad\quad\quad\quad\quad\quad\quad\quad\quad\quad\quad\quad\quad|$$
$$\quad\quad\quad\quad\quad\quad\quad\quad\quad\quad\quad\quad\quad CH$$
$$\quad\quad\quad\quad\quad\quad\quad\quad\quad\quad\quad\quad\quad\|$$
$$\quad\quad\quad\quad\quad\quad\quad\quad\quad\quad\quad\quad\quad CH_2$$

PhO—C(=O)—NH—(CH$_2$)$_6$—NH—C(=O)—OPh $$CH_2=CHCOO(CH_2CH_2O)_{2-6}CH_2=CH_2 \quad (v)$$

(vi) bis-imidazolyl carbonyl benzene tris-imidazolyl carbonyl benzene bis-imidazolyl diacyl (CH$_2$)$_{4-8}$ with pyrrolidinyl substituent (vii) $ClCH_2COOH$, $ClCH_2COOCH_3$, $ClCH_2COOC_2H_5$, $ClCH_2COOCH_2CH=CH_2$, $ClCH_2COO$—C$_6$H$_5$ (B) High-molecular-weight internal crosslinking agents containing at least 40 mole% of at least one recurring unit selected from $$-CH_2-\underset{\underset{COO-CH_2-CH(OH)-CH_2-X_{17}}{|}}{\overset{A_{12}}{C}}- \quad (i)$$

$$-CH_2-\underset{\underset{COO-A_{13}}{|}}{\overset{A_{12}}{C}}- \quad (ii)$$

$$-CH_2-\underset{\underset{\underset{CH_2-(CH_2)_d}{O}}{\underset{C=O, \text{ and}}{|}}}{\overset{A_{12}}{\underset{|}{C}}}- \quad (iii)$$

$$-CH_2-\underset{\underset{\underset{N-pyrazolyl}{C=O}}{|}}{\overset{A_{12}}{\underset{|}{C}}}- \quad (iv)$$

wherein $X_{17}$ represents a halogen atom, $A_{12}$ is a hydrogen atom or a methyl group, $A_{13}$ represents a hydrogen atom or an alkyl group having 1 to 4 carbon atoms, an allyl group, an aralkyl group having 7 to 10 carbon atoms, or a phenyl group, and d is 1 or 2.

These high-molecular-weight compounds may consist only of at least one of such recurring units, or may contain another recurring unit. Examples of the other recurring unit which may exist are as follows:

$$-CH_2-CH-\quad,\quad -CH_2CH-\quad,\quad -CH_2CH-$$
$$\quad\quad\;|\quad\quad\quad\quad\quad\quad\;|\quad\quad\quad\quad\quad\quad\;|$$
$$\quad\quad C=O\quad\quad\quad\quad C=O\quad\quad\quad\quad C=O$$
$$\quad\quad\;|\quad\quad\quad\quad\quad\quad\;|\quad\quad\quad\quad\quad\quad\;|$$
$$\quad\quad N(CH_3)_2\quad\quad\;NH_2\quad\quad\;N(CH_2CH_3)_2$$

$$-CH_2CH-\;,\;-CH_2-CH-\;,\;\text{piperidinium-CH}_2-\;Cl^\ominus$$
$$\quad\;|\quad\quad\quad\quad\quad\;|$$
$$\quad C=O\quad\quad\quad N\text{-pyrrolidone}$$
$$\quad\;|$$
$$\quad NHCH_2OH$$

$$\text{piperidinium-CH}_2-SO_2-\;,\;-CH_2CH-\;,\;-CH_2CH-$$
$$\quad\quad\quad\quad\quad\quad\quad\quad\quad\quad\quad\quad\quad\;|\quad\quad\quad\quad\;|$$
$$\quad\quad\quad\quad\quad\quad\quad\quad\quad\quad\quad\quad\;OCH_3\quad\;OC_2H_5$$

$$-CH_2CH-\;,\;-CH_2CH-\;,\;-CH-CH-\;,\;-CH-CH-$$
$$\quad\;|\quad\quad\quad\quad\;|\quad\quad\quad\;|\quad\quad\;|\quad\quad\;|\quad\quad\;|$$
$$\quad OCCH_3\;\;OH\;\;COOH\;\;COOH\;\;COOCH_3$$
$$\quad\|$$
$$\quad O$$

Thus, examples of the high-molecular-weight internal crosslinking agents include those which contain at least 30 mole%, more preferably at least 50 mole%, of at least one of the following recurring units.

$$-CH_2CH-\quad\quad\;,\quad -CH_2\overset{CH_3}{\underset{|}{C}}- \quad (i)$$
$$\quad\;|\quad\quad\quad\quad\quad\quad\quad\;|$$
$$\quad COOCH_2CHCH_2Cl\quad COOCH_2CHCH_2Cl$$
$$\quad\quad\quad\;|\quad\quad\quad\quad\quad\quad\quad\quad\quad\;|$$
$$\quad\quad\quad OH\quad\quad\quad\quad\quad\quad\quad\quad\;OH$$

$$-CH_2CH-\;,\;-CH_2\overset{CH_3}{\underset{|}{C}}-\;,\;-CH_2CH- \quad (ii)$$
$$\quad\;|\quad\quad\quad\quad\;|\quad\quad\quad\quad\;|$$
$$\quad COOCH_3\;\;COOCH_3\;\;COOCH_2CH_2OH$$

$$-CH_2\overset{CH_3}{\underset{|}{C}}-$$
$$\quad\;|$$
$$\quad COO(CH_2CH_2O)_z-H$$

-continued

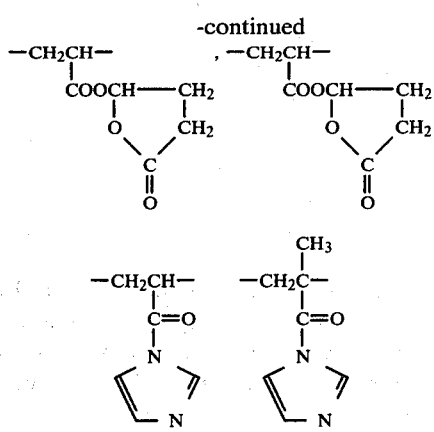

Especially preferred high-molecular-weight internal crosslinking agents are those containing the following recurring units.

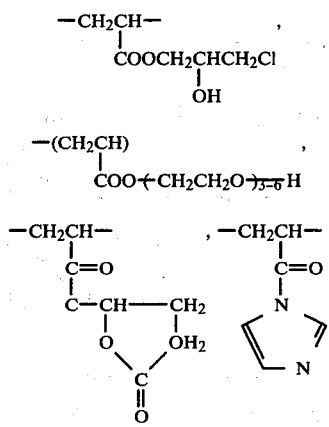

Especially preferred internal crosslinking agents for use in this invention are those which react with the active amino groups in the amino polymer to form a socalled hydrophilic hydrogel. If the hydrophobicity of the internal crosslinking agent (more strictly, the hydrophobicity of the crosslinked structure formed by the reaction of the crosslinking agent with the active amino groups) is too high, the anchor layer (located between the microporous substrate and the crosslinked active layer formed by interfacial crosslinking) acts as an internal barrier to water permeation, resulting in a reduction in the water flux of the membrane. In this sense, the internal crosslinking agent preferably has high hydrophilicity, and aliphatic compounds and alicyclic compounds are preferred to aromatic compounds, the aliphatic compounds being especially preferred.

Examples of internal crosslinking agents which are preferred from this standpoint include ethylene glycol dichlorohydrin, glycerol dichlorohydrin, glycerol trichlorohydrin, sorbitol dichlorohydrin, sorbitol trichlorohydrin, sorbitol tetrachlorohydrin, dimethyl tartrate and diethyl tartrate.

The amino polymer and the internal crosslinking agent which have been described in detail hereinabove are pre-mixed and used in the form of a solution. The solution does not denote a uniform clear solution alone, and may include an emulsion if a film can be prepared from the emulsion by means to be described.

A solvent system consisting of at least one solvent selected from water and water-miscible organic solvents having a boiling point of not more than 140° C., preferably not more than 120° C., is suitable as the solvent used to form such a solution. The solvent system should be selected such that it does not substantially swell or dissolve the microporous substrate to be described. Examples of preferred solvents are (i) water, (ii) a low alcohol such as methanol, ethanol and propanol, (iii) a ketone such as acetone, methyl ethyl ketone and diethyl ketone, and (iv) a lower carboxylic acid such as formic acid, acetic acid and propionic acid.

These solvents can be used either alone or as a mixture of two or more. Water, the lower alcohols, and the mixtures thereof are preferred. Water is especially preferred.

The mixing ratio between the amino polymer and the internal crosslinking agent are not critical, and can generally be changed widely depending upon the types of the polymer and/or internal crosslinking agent used. Generally, it can be determined according to the equivalent weight of the active amino groups contained in the amino-polymer. The internal crosslinking agents can be mixed in such a ratio that the ratio of the equivalent weight of the functional groups in the internal crosslinking agent to that of the active amino groups in the amino polymer is generally 0.05-1:1, preferably 0.1-0.7:1, more preferably 0.2-0.5:1.

The concentration of the amino polymer in the solution is not critical, and can be varied widely depending upon the type of the polymer used, and the properties required of the final membrane, etc. Advantageously, it is generally at least 0.5% by weight, preferably 1.0 to 5.0% by weight, especially preferably 1.5 to 3.0% by weight.

The solution so prepared may, if required, include a monofunctional compound containing only one functional group ($F_1$) of the type exemplified above per molecule. This can lead to the improvement of the hydrophilicity, flexibility or oxidation resistance of the resulting semipermeable membrane.

Examples of the monofunctional compound that can be used for this purpose include ethylene carbonate

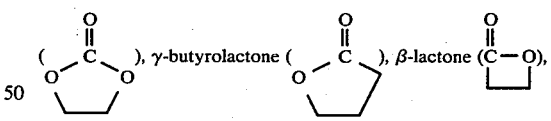

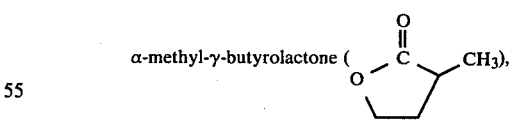

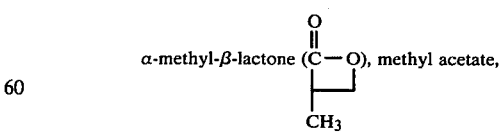

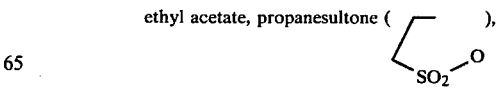

ethyl ortho-formate [CH(OC$_2$H$_5$)$_3$], ethyl methylcarbamate, acetic acid and propionic acid.

The monofunctional compounds may be used singly or as a mixture of two or more. The amount of the monofunctional compound is used in such an amount that the concentration of the functional group is 0.1 to 0.7 equivalent, preferably 0.2 to 0.5 equivalent, per equivalent of the active amino groups in the amino polymer. Usually, it is used in a smaller amount than the internal crosslinking agent.

As required, an acid acceptor may be added to the solution in order to promote the crosslinking reaction and control the concentration of the ammonium salt group. When the functional group ($F_2$) of the crosslinking agent used in the interfacial crosslinking reaction to be described is, for example, an acid chloride group, the acid acceptor accepts an acid released as a result of the crosslinking reaction, and promotes the reaction. Inorganic and organic basic compounds are used as the acid acceptor. Typical examples are alkaline or alkaline earth metal hydroxides such as sodium hydroxide, potassium hydroxide and calcium hydroxide and alkali or alkaline earth metal carbonates such as sodium bicarbonate, sodium carbonate and calcium carbonate, and amine compounds such as pyridine and piperazine. The amount of the acid acceptor is generally 0.2 to 1.5 moles, preferably 0.5 to 1.0 mole, per mole of the active amino groups in the amino polymer.

The solution of the amino polymer and the internal crosslinking agent so prepared is coated on, or impregnated in, a microporous substrate to be described in a manner known per se to form thereon a thin layer containing the polymer and the internal crosslinking agent. The resulting thin film needs not to have selfsupporting property, and may contain the aforesaid additives and solvent.

Substrates that can be used may be any of the types conventionally used in a reverse osmosis process. They include porous glass, sintered metals, ceramics, and organic polymeric materials such as cellulose esters, styrene resins, vinyl butyral resins, polysulfone, chlorinated polyvinyl chloride, etc. described in U.S. Pat. No. 3,676,203. Polysulfone film has been found to be a particularly effective support material for the membranes of the invention, and chlorinated polyvinyl chloride is another very effective support material. Preparation of polysulfone microporous substrate is described in "Office of Saline Water Research and Development Progress Report No. 359, Oct., 1968".

These substrate preferably have a surface pore size of generally 100 to 1000 Å, but are not limited to these specific sizes. Depending upon the use of the final membrane product, surface pores ranging in size from about 50 Å to about 5000 Å may be acceptable.

The substrate may be of an isotropic structure or an anisotropic structure, desirably of the latter structure. When the membrane constant of the substance is less than $10^{-4}$ g/cm$^2$.sec.atm, the water permeability of the substrate is too low, and when it is more than 1 g/cm$^2$.sec.atm, the salt rejection tends to be extremely low. Accordingly, preferred membrane constants are 1 to $10^{-4}$ g/cm$^2$.sec.atm, and the best results are obtained with a membrane constant of $10^{-1}$ to $10^{-3}$ g/cm$^2$.sec.atm. The term "membrane constant", as used herein, denotes the amount of pure water which permeates the membrane under a pressure of 2 kg/cm$^2$, and is expressed in g/cm$^2$. sec.atm.

Preferably, the substrate used is reinforced at its back with a woven or non-woven cloth, etc. Examples of the woven or non-woven cloth are those of polyethylene terephthalate, polystyrene, polypropylene, nylon or vinyl chloride resins.

To form the thin layer containing the amino polymer and the internal crosslinking agent on the microporous substrate, the microporous substrate is treated with the aforesaid solution containing the amino polymer and the internal crosslinking agent.

The treatment can be performed by coating at least one surface of the substrate with a solution of the base polymer by a suitable method such as solution coating, brush coating, spraying, wick coating or roll coating; or by immersing the substrate in a solution of the base polymer.

The substrate so treated by coating or immersion is then subjected to a drain treatment. The drain treatment can be carried out generally at room temperature for 1 to 30 minutes, preferably 5 to 20 minutes. This results in the formation of a pseudo-thin film layer comprising the amino polymer and having a total thickness of about 500 to about 20,000 Å, preferably about 1,000 to about 10,000 Å, on the surface of the substrate. The preudothin film layer so formed can be air-dried, as required. It is very desirable that the pseudo-thin film layer should contain at least 10% by weight, preferably 20 to 70% by weight of the amino polymer and at least 20% by weight, preferably 30 to 80% of the aforesaid solvent remaining therein.

The substrate having the thin layer formed thereon is then subjected to interfacial crosslinking reaction using a crosslinking agent containing at least two functional groups ($F_2$) capable of easily reacting with the primary or secondary amino groups or both in the amino polymer. As a result, a thinner crosslinked layer (located outwardly of the permselective layer) is formed on the surface of the pseudo-thin layer.

The functional groups ($F_2$) which can be present in this highly reactive crosslinking agent are functional groups capable of easily reacting with the primary or secondary amino groups or both in the amino polymer, and specifically include carbonyl halide groups (-CO-Hal), sulfonyl halide groups (-SO$_2$Hal), carboxylic acid anhydride groups

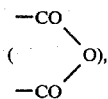

sulfonic acid anhydride groups

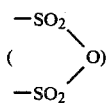

and derivative groups of carboxylic acids and sulfonic acids having equivalent reactivity to those halide and anhydride groups. In these groups, Hal represents a halogen atom, preferably chlorine and bromine.

Examples of the carboxylic and sulfonic acid derivative groups are —COO—SO$_2$CH$_3$ and —COO—PO—(OCH$_3$)$_2$.

The polyfunctional compound used in this invention may contain at least two, preferably two or three, functional groups (F₂) per molecule. The two or more functional groups (F₂) present in one molecule may be the same or different. Generally, the polyfunctional compound desirably has a cyclic structure, and may be of any of aromatic, heterocyclic and alicyclic structures. It has been found that aromatic polyfunctional compounds are especially effective for the objects of this invention.

Aromatic polyfunctional compounds that can be used advantageously in this invention are mononuclear or polynuclear (binuclear, in particular) compounds which contain at least two, preferably 2 or 3, functional groups bonded to the aromatic nucleus and 6 to 20 carbon atoms, preferably 6 to 15 carbon atoms. Preferably, substituents other than the aforesaid functional groups should not be present on the aromatic ring. The aromatic ring, however, may have 1 or 2 groups which do not substantially affect the crosslinking reaction, such as a lower alkyl group, a lower alkoxy group, a halogen atom, etc.

An especially preferred group of such aromatic polyfunctional compounds includes compounds of the following formula

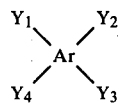

wherein Ar represents a benzene ring, a naphthalene ring, or the ring

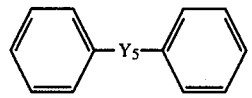

in which Y₅ represents —CH₂—,

—O—, SO₂— or —CO—, Y₁, Y₂, Y₃ and Y₄, independently from each other, represent a hydrogen atom, a carbonyl halide or sulfonyl halide group proved that at least two of Y₁, Y₂, Y₃ and Y₄ represent groups other than hydrogen, or Y₁ and Y₂ or Y₃ and Y₄ respectively taken together represent a carboxylic acid anhydride group or a sulfonic acid anhydride group; it is especially desirable that Y₁, Y₂, Y₃ and Y₄ be selected from carbonyl halide and sulfonyl halide groups. Typical examples of the aromatic polyfunctional compounds used as the crosslinking agent are shown below.

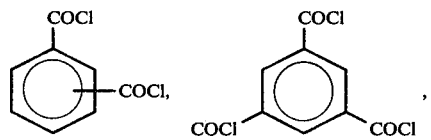

-continued

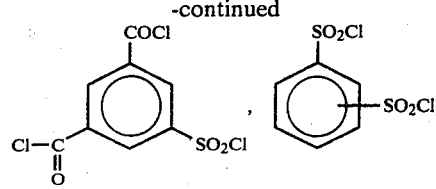

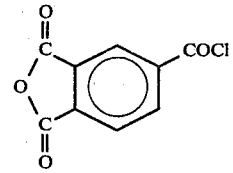

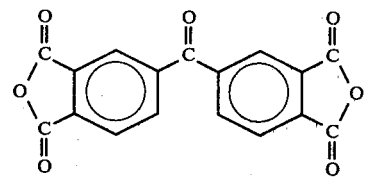

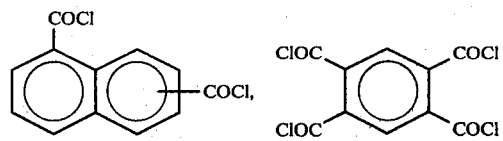
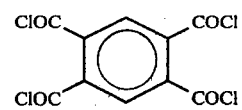

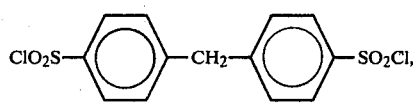

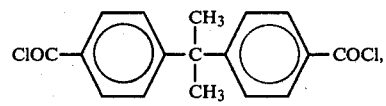

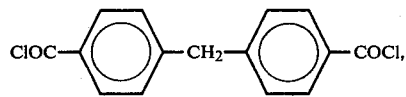

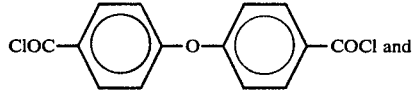 and

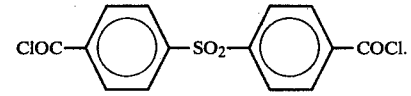

Especially advantageous aromatic polyfunctional compounds are isophthaloyl chloride, terephthaloyl chloride, trimesiloyl chloride and 5-chlorosulfonylisophthaloyl chloride.

It has been found that the ion-permselectivity and/or water-flux properties of the finally obtained membrane can be improved by using trifunctional aromatic compounds rather than difunctional ones when they are used singly, and by using a combination of a difunctional aromatic compound and a trifunctional aromatic compound when they are used in combination. Thus, especially preferred polyfunctional aromatic compounds to be used in the present invention are trifunctional aromatic compounds, and mixtures of difunctional aromatic compounds and trifunctional aromatic compounds. When a mixture of a difunctional aromatic compound and a trifunctional aromatic compound is used, the mixing ratio between them is not critical.

Crosslinking of the aforesaid pseudo-thin film can generally be performed by interfacially contacting it with a solution of the aforesaid polyfunctional aromatic compound. The solvent used to dissolve the polyfunctional aromatic compound is selected from those compounds which are incompatible with the aforesaid solution containing the amino polymer and do not substantially dissolve or swell the microporous substrate. Examples of such solvents include hydrocarbons such as n-hexane, n-heptane, n-octane, cyclohexane, n-nonane and n-decane.

The interfacial crosslinking reaction is carried out under controlled conditions such that the interfacially crosslinked polymer zone on the surface of the thin film on the microporous substrate after the crosslinking reaction contains at least 0.5 milliequivalents, preferably 1.0 to 6.0 milliequivalents, more preferably 1.0 to 5.0 milliequivalents, per gram of the interfacially crosslinked polymer (dry), of an ammonium salt group and at least 0.05 milliequivalents, preferably 0.1 to 3.0 milliequivalents, per gram of the interfacially crosslinked polymer (dry), of the group —YOM in which Y and M are as defined with regard to formula (I), and the equivalent ratio of the ammonium salt group to the group —YOM is in the range of from 20:1 to 1:2, preferably from 15:1 to 2:3, more preferably from 10:1 to 1:1.

The ammonium salt groups contained in the interfacially crosslinked polymer zone include not only the ammonium salt group inherently contained in the starting amino polymer, but also those which are formed by the reaction with the amine in the starting polymer of hydrogen halides liberated as a result of crosslinking reaction of —COX or —SO$_2$X in the crosslinking agent with the amine, or reaction of it with water, etc.

On the other hand, the group —YOM is formed by hydrolysis of —COX, —SO$_2$X,

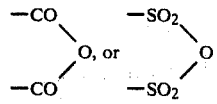

in the crosslinking agent, and by the bonding of M+ present at this time, such as H+, an alkali metal ion, an alkaline earth metal ion or an ammonium ion thereto, it is the group —YOM is introduced into the interfacially crosslinked polymer zone.

It is important therefore that in the interfacial crosslinking reaction, at least one unreacted functional group which does not participate in the crosslinking reaction be left in at least a part of the polyfunctional aromatic compound bonded to the amino polymer as a result of this reaction.

The most important factor for performing the interfacial crosslinking reaction so that the contents of the ammonium salt groups and the group —YOM in the resulting interfacially crosslinked polymer zone and the ratio between them fall within the aforesaid range is the concentration of the polyfunctional aromatic compound in its solution to be contacted with the pseudo-thin film.

The concentration of the aromatic compound in the solution containing it needs to be varied depending upon the type of the amino polymer to be crosslinked, etc. Generally, when an amino polymer substantially free from both a tertiary amino group and an ammonium salt group is used as the starting amino polymer, it is desirable to contact the pseudo-thin film with a solution containing the polyfunctional aromatic compound in a concentration of 2 to 10% by weight, preferably 4 to 8% by weight, more preferably 5 to 8% by weight. When the starting amino polymer is an amino polymer containing a tertiary amino group and/or an ammonium salt group in a concentration of generally 1 to 18 milliequivalent, preferably 2 to 12 milliequivalents, per gram of the dry polymer, it is desirable to contact the pseudo-thin film with a solution containing the polyfunctional aromatic compound in a concentration of 0.2 to 4.0% by weight, preferably 0.3 to 3.0% by weight, more preferably 0.5 to 2.0% by weight.

When the amino groups in the polymers are predominantly of active amino groups, the amount of an ammonium salt group formed by the reaction of the hydrogen halide freed as a result of crosslinking reaction with the amino groups in the polymer can be increased by greatly increasing the concentration of the crosslinking agent. In this case, it is preferred not to use a large amount of the acid acceptor in the crosslinking reaction.

When the polymer initially has an ammonium salt group, the concentration of the crosslinking agent needs not to be increased so much, and may be adjusted to a suitable concentration in view of the desired rejection of organic matter. If the concentration of active amino groups in the starting polymer is low in this case, it is preferred to perform crosslinking exactly by using an acid acceptor during the crosslinking reaction.

Conveniently, the crosslinking is accomplished on the interface between the thin film layer and the solution of the polyfunctional aromatic compound by immersing the thin film layer in the solution of the polyfunctional aromatic compound. In order to promote this crosslinking reaction, it is possible to include a crosslinking accelerator into the thin film layer or into the solution of the polyfunctional aromatic compound. Suitable accelerators are, for example, alkali metal or alkaline earth metal hydroxides; sodium phosphate; amino compounds such as pyridine, and piperazine; surface-active agents; and sodium acetate.

The interfacial crosslinking reaction between the surface of the thin film layer and the polyfunctional aromatic compound can be carried out at about room temperature, preferably 20° to 50° C., for a period of 10 seconds to 10 minutes, preferably 30 seconds to 5 minutes. When the thin film layer contains the internal crosslinking agent, the interfacial crosslinking reaction should be carried out at a temperature lower than the temperature at which the internal crosslinking agent substantially reacts. This interfacial reaction can be performed so that it takes place largely on the surface of the thin film layer, and it is not necessary to reduce the water sensitivity of the internal regions of the film.

Then, the thin film supported on the substrate may optionally be subjected to a drain treatment to drain the excess of the polyfunctional compound solution for 10 seconds to 2 minutes. If further required, it may be dried at a low temperature, usually at about 20° to 50° C.

The thin film on the substrate which has thus been subjected to the interfacial crosslinking reaction is then subjected to hydrolysis in order to convert the functional group remaining unreacted in the aromatic polyfunctional compound bonded to the amino polymer into a cation exchange group (—YOM). Reagents which can be advantageously used in the hydrolysis include organic bases such as alkali metal hydroxides, alkaline earth metal hydroxides, alkali metal carbonates, alkaline earth metal bicarbonates and ammonium hydroxide. The hydrolysis reaction can also be carried out by using an aqueous solution of a neutral salt such as an alkali metal halide or an alkaline earth metal halide. The hydrolysis can be achieved by simply dipping the resulting thin film in an aqueous solution containing such a hydrolysis reagent at room temperature, or by simply dipping it in water.

The amphoteric ion-permeable composite membrane obtained through the above process steps can be directly used in practical applications.

The foregoing procedure gives an amphoteric ion-permeable composite membrane composed of (1) a microporous substrate produced by forming a thin layer comprising an active amino group-containing polymer containing 1.0 to 23 milliequivalents/g, as amino equivalent, of an active amino group selected from primary and secondary amino groups and 0 to 18 milliequivalents/g, as amino equivalent, of a tertiary amino group and/or an ammonium salt group per molecule with the total amino content thereof being in the range of 2.0 to 23 milliequivalents/g on a microporous substrate and then contacting the thin layer on the substrate interfacially with a polyfunctional aromatic compounds containing at least two functional groups selected from carbonyl halide groups, sulfonyl halide groups, carboxylic acid anhydride groups, sulfonic acid anhydride groups and derivative groups of carboxylic acids and sulfonic acids having equivalent reactivity to the aforesaid halide and anhydride groups, and (2) supported on the substrate (1), a thin amphoteric ion-exchange film formed of the active amino group-containing polymer which has been interfacially crosslinked at least at the surface portion of the thin film; the interfacially crosslinked polymer zone of the thin film containing at least one structural unit of the formula

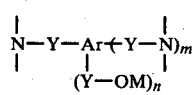

(I)

wherein Ar represents an aromatic ring, Y represents CO or SO$_2$ provided that (m+n+1) groups Y bonded to the group Ar are identical or different, M represents an atom or atomic grouping capable of being split off as a cation, and m and n each represent an integer of 0 or more provided that m+n=1–3, said polymer zone further containing a structural unit of formula (I) in which m is not zero when it contains a structural unit of formula (I) in which m is zero, and further containing a structural unit of formula (I) in which n is not zero when it contains a structural unit of formula (I) in which n is zero, and additionally containing at least 0.5 milliequivalents/g, based on the crosslinked polymer (dry), of an ammonium salt group as a cation-exchange group and at least 0.05 milliequivalents/g of the crosslinked polymer (dry) of the group —YOM in formula (I) as an anion-exchange group, the equivalent ratio of the ammonium salt group to the group —YOM being in the range of from 20:1 to 1:2.

The interfacially crosslinked polymer zone of the thin film may can contain various structural units depending upon the type of the polymer and/or polyfunctional aromatic compound used, etc., but should contain at least one of crosslinking structural units of the following formulae (I-1), (I-2) and (I-3). In the following structural units, nitrogen

is derived from the active amino groups in the starting amino polymer, and the group —YOM is derived from a functional group in the aromatic polyfunctional compound which has not participated in the crosslinking but remained unreacted.

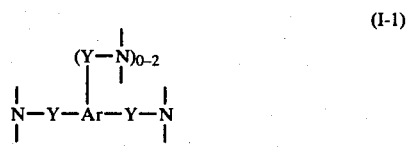

(I-1)

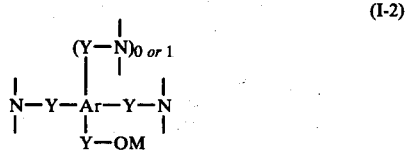

(I-2)

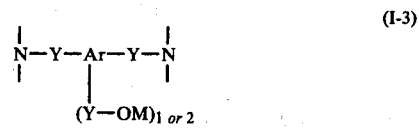

(I-3)

The interfacially crosslinked polymer zone may further contain a structural unit of the following formula in addition the above crosslinked structural units.

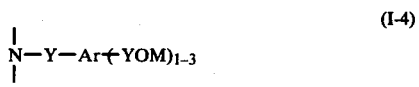

(I-4)

In the above formulae (I-1) to (I-4), Ar, Y and M are as defined hereinabove, and Ar is preferably a benzene ring. Specific examples of the atom or atomic grouping (M) capable of being split off as a cation include H$^+$, alkali metal ions such as Na$^+$, K$^+$ and Li$^+$, alkaline earth metal ions such as Ca$^{++}$ and Mg$^{++}$, and ammonium ions such as —NH$_4^+$ and —N(CH$_3$)H$^+$.

Some specific structures assumed of such a structural unit portion are as follows:

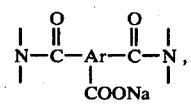

-continued

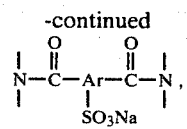

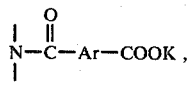

When only the unit of formula (I-1) is present as a crosslinked unit in the interfacially crosslinked polymer zone, the interfacially crosslinked polymer zone must contain the unit of formula (I-4).

The crosslinked structural units should be present in amounts sufficient to render the interfacially crosslinked polymer zone substantially water-insoluble. Units containing the group —YOM, i.e. the units of formulae (I-2), (I-3) and (I-4) may be present in a total amount of at least 0.05 milliequivalents, preferably 0.1 to 5.0 milliequivalents, more preferably 0.2 to 3.0 milliequivalents, per gram of the interfacially crosslinked polymer (dry).

The interfacially crosslinked polymer zone contains ammonium salt groups for imparting cation exchangeability to the membrane. The ammonium salt groups include not only an ammonium salt group which may be inherently possessed by the starting amino polymer but also an ammonium group salt group formed by the reaction of a hydrogen halide liberated during the interfacial crosslinking reaction with an active amino group in the amino polymer which has not been involved in the crosslinking reaction and/or a tertiary amino group which may be present in the amino polymer. Specific examples of such an ammonium salt group are the same as those of formulae (VIII-1) to (VIII-14) given hereinabove.

The ammonium salt groups may be present in an amount of at least 0.5 milliequivalents, preferably 0.5 to 8.0 milliequivalents, more preferably 1.0 to 5.0 milliequivalents, per gram of the interfacially crosslinked polymer (dry).

The ammonium salt groups and the group —YOM may be present in such proportions that the equivalent ratio of the ammonium salt groups to the group —YOM is in the range of from 20:1 to 1:2 preferably from 15:1 to 2:3, more preferably from 10:1 to 1:1.

The thin film having such an interfacially crosslinked polymer zone at least on its surface portion may have a thickness of generally 500 to 20,000 Å, preferably 1,000 to 10,000 Å.

The amphoteric ion-permeable composite membrane thus provided by the present invention may have an NaCl rejection of generally at most 40%, preferably at most 30%, more preferably at most 25%, and a sucrose rejection of generally at least 80%, preferably at least 85%, more preferably at least 90%.

In the present specification and the appended claims, the "NaCl rejection" and the "sucrose rejection" are as defined below.

$$\text{NaCl rejection (\%)} = \left(1 - \frac{\text{NaCl concentration in permeating water}}{\text{NaCl concentration in the test solution}}\right) \times 100$$

$$\text{Sucrose rejection (\%)} = \left(1 - \frac{\text{Sucrose concentration in permeating water}}{\text{Sucrose concentration in the test solution}}\right) \times 100$$

Advantageously, the composite membrane of this invention has a Q, defined by the following equation, of at least 150, preferably at least 160.

Q=2×(sucrose rejection in %)−(NaCl rejection in %)

The composite membrane so obtained can be directly used in applications to be described. Desirably, however, subsequent to the interfacial crosslinking reaction, the composite membrane is drained, and immediately then, heat-treated to improve the properties such as the durability and organic matter rejection, of the membrane. When the starting amino polymer is self-gelling, or the aforesaid internal crosslinking agent is used to produce the membrane, the aforesaid heat-treatment leads to self-gellation of the thin film or the internal crosslinking of the membrane. As a result, a composite membrane having improved properties such as durability, oxidation resistance, pressure compaction resistance and organic matter rejection can be obtained.

The heat-treatment can be performed at a temperature of generally at least 70° C., preferably 70° to 150° C., more preferably 90° to 130° C., for a period of at least 1 minute, preferably 1 to 60 minutes, more preferably 5 to 30 minutes.

The stability of the membrane can be improved by this heat-treatment, as stated hereinabove. The present inventors have ascertained that the amounts of the ammonium salt groups and the group —YOM in the interfacially cross-linked polymer zone in this heat-treated membrane are much the same as those of a composite membrane produced by using an amino polymer having no self-gelling ability as the starting polymer without using the internal crosslinking agent.

It is presumed that in a preferred embodiment, the amphoteric ion-permeable composite membrane obtained as a result of the heat-treatment contains 0.5 to 8 milliequivalents/g of the crosslinked polymer (dry) of ammonium salt groups as anion-exchange groups and 0.05 to 5 milliequivalents/g of the crosslinked polymer (dry) of the group —YOM in formula (I) as an cation-exchange group with the equivalent ratio of the ammonium salt groups to the group —YOM being in the range of from 20:1 to 1:2. The composite membrane thus obtained has excellent selective ion-permeability as shown in Examples given hereinbelow, and can permit high-speed selective permeation of water and an inorganic ionic compound from a mixed solution of the inorganic ionic compound and organic matter in an aqueous medium.

Accordingly, the amphoteric ion-permeable composite membrane is useful in separation or concentration of a water-soluble inorganic compound and an organic compound (e.g., NaCl and sucrose) having an equivalent molecular size, or concentration of ionic compound by pressure dialysis. Thus, it exhibits characteristics not seen in conventional reverse osmosis membranes or ultrafiltration membranes. The industrial significance of such amphoteric ion-permeable composite membrane is very great.

The following Examples illustrate the present invention in greater detail.

Reverse osmosis testing method

Reverse osmosis test was carried out in an ordinary continuous pump-type reverse osmosis device using a mixed aqueous solution of 1% sodium chloride and 3% sucrose a pH of 7.0 and a temperature of 25° C. The operating pressure was 20 kg/cm$^2$.G.

Salt rejection

The salt rejection (%) is a value calculated from the following equation.

$$\text{Salt rejection (\%)} = \left(1 - \frac{\text{NaCl concentration in permeating water}}{\text{NaCl concentration in the test solution}}\right) \times 100$$

Sucrose rejection

The sucrose rejection (%) is a value calculated from the following equation.

$$\text{Sucrose rejection (\%)} = \left(1 - \frac{\text{Sucrose concentration in permeating water}}{\text{Sucrose concentration in the test solution}}\right) \times 100$$

Referential Example 1

Production of a microporous polysulfone substrate:

A Dacron non-woven fabric (basis weight 180 g/m$^2$) was fixed to a glass plate. Then, a solution containing 12.5% by weight of polysulfone, 12.5% by weight of methyl Cellosolve and the remainder being dimethyl formamide was cast onto the fabric in a layer having a thickness of about 200 microns. Immediately, the polysulfone layer was gelled in a water bath kept at room temperature to form a non-woven fabric-reinforced microporous polysulfone membrane.

The resulting microporous polysulfone layer had a thickness of about 40 to about 70 microns and had an anisotropic structure. By observation with an electron microscope, the surface of the microporous layer was found to contain numerous micropores with a size of 50 to 600 Å.

The microporous substrate had a pure water flux (membrane constant) of about 3.0 to 7.0×10$^{-2}$ g/cm$^2$.sec.atm.

Referential Example 2

Method for measuring the amine equivalent and the ammonium salt equivalent:

The total amine equivalent is measured by the perchloric acid-acetic acid titration method described, for example, in J. B. Conant and N. F. Hall, J. Am. Chem. Soc., 49, 3047 (1927). The determination of the tertiary amine equivalent is made by the "acetylation-perchloric acid method" described, for example, in C. D. Wagner, R. D. Brown and E. D. Peters, J. Am. Chem. Soc., 69, 2609 (1947).

The equivalent weight of (primary amine plus secondary amine) is calculated by subtracting the tertiary amine equivalent from the total amine equivalent.

The ammonium salt equivalent was determined by dissolving a sample containing about 1 milliequivalent of an ammonium salt in 50 ml of 1 N sodium hydroxide solution, and titrating the solution with a 0.1 N silver nitrate solution.

Referential Example 3

Method for measuring the ion exchange capacity:

A microporous polysulfone membrane (0.1 m$^2$) was dipped for a predetermined period of time in an aqueous solution of a polyamine, and dried. The dried membrane was then dipped in a solution of a crosslinking agent, and then fully dried at room temperature. The dried membrane was then dipped in chloroform to dissolve the polysulfone layer, and the crosslinked polymer layer was separated by filtration. The crosslinked polymer layer was stirred for 1 hour in 500 ml of chloroform, then filtered, and washed with chloroform to remove the polysulfone completely. Then, the crosslinked polymer was washed with methanol to remove the uncrosslinked polyamine and the unreacted crosslinking agent. The resulting crosslinked polymer was stirred for 1 hour in a 1 N aqueous solution of hydrochloric acid, filtered, and washed with water to remove the hydrochloric acid. It was then dried overnight in a vacuum dryer at 100° C. About half of the dried polymer was precisely weighed, and stirred for 1 hour in 100 ml of a 0.01 N sodium hydroxide solution. A part of the resulting solution was titrated with 0.01 N hydrochloric acid and the amount of sodium hydroxide consumed was measured. The consumed amount is designed as a (meq./g-dried crosslinked layer).

Using the remaining solution, its chlorine content was determined by titration with 0.01 N silver nitrate. The chlorine content is designated as b (meq./g-dried crosslinked layer).

Separately, the remaining dried crosslinked layer was precisely weighed, and dried for 1 hour in 100 ml of 1 N sodium hydroxide. The chlorine content of the polymer was determined by titration with 0.01 N silver nitrate. The chlorine content is designated as c (meq./g-dried cross-linked layer).

The anion exchange capacity is represented by c meq./g-dried crosslinked layer, and the cation exchange capacity is represented by (a-b) meq./g-dried crosslinked layer. The value (a-b)/c is defined as the ion exchange capacity ratio.

Referential Example 4

Methods for measuring the degree of water insolubility of the polyamino polymer:

A predetermined amount of a polyamino polymer was added to 100 parts of water, and they were stirred at room temperature to form a solution. When it is desired to determine the effect of adding the polyfunctional compound, a predetermined amount of it is further added to the solution, and the mixture is stirred at room temperature to form a solution.

The resulting polyamino polymer solution in a predetermined concentration was charged into an autoclave, and the temperature was raised rapidly to a predetermined point under pressure. The solution was maintained at this temperature for 30 minutes to gel the polyamino polymer and then quenched to room temperature.

The polymer solution containing the gelled polymer was filtered to separate the dissolved polyamino polymer. The concentration obtained was washed with 100 parts of water or alcohol at 70° C. and dried. The weight of the gelled polymer was then measured.

The percentage of the weight of the gelled polymer based on the weight of the polyamino polymer used (when the polyfunctional compound is used, its weight is added) is defined as the degree of water insolubility at the above mentioned temperature of the polyamino polymer.

EXAMPLE 1

Twenty parts of a 30% aqueous solution of polyethyleneimine (P-1000, a tradename for a product of Nippon Shokubai Kagaku Kogyo Co., Ltd.; average molecular weight 70000, primary and secondary amine equivalent 16.7 meq./g, tertiary amine equivalent 5.2 meq./g) and 566 parts of water were mixed, and 14 parts of a 1 N aqueous solution of hydrochloric acid was added. The mixture was stirred to form an amino polymer solution.

A non-woven fabric-reinforced polysulfone porous membrane (with a polysulfone membrane thickness of about 60 microns and a membrane constant of $5.2 \times 10^{-2}$ g/cm$^2$.sec. atm.) obtained by the method described in Referential Example 1 was immersed in this solution at room temperature for 2 minutes. The membrane was withdrawn and caused to stand vertical to allow the solution to drain for 20 minutes. The treated membrane was immersed in a 1.0% n-hexane solution of trimesoyl chloride as a crosslinking agent. The membrane was taken out, and dried at room temperature.

A sample having an area of 9.6 cm$^2$ was cut off from the resulting membrane, and subjected to the reverse osmosis test described hereinabove. It showed a water flux of 75 liters/m$^2$.hr, a salt rejection of 12.4%, and a sucrose rejection of 95.3%.

The ion exchange capacity of the crosslinked layer of the remaining membrane was measured by the method described hereinabove. It showed an anion exchange capacity of 4.1 meq./g, a cation exchange capacity of 1.3 meq./g, and an ion exchange capacity ratio of 0.32.

COMPARATIVE EXAMPLES 1 AND 2

Example 1 was repeated except that hydrochloric acid was not added, and each of the crosslinking agent shown in Table 1 was used. The properties of the resulting membranes are shown in Table 1.

TABLE 1

| Comparative Example | Crosslinking agent Type | Concentration (%) | Cation exchange capacity (meq./g) | Anion exchange capacity (meq./g) | Ion exchange capacity ratio | Water flux (liter/m$^2$.hr) | NaCl rejection (%) | Sucrose rejection (%) |
|---|---|---|---|---|---|---|---|---|
| 1 | IPC (*1) | 1 | 0.01 | 4.43 | 0.002 | 9.3 | 98.4 | 99.6 |
| 2 | TMC (*2) | 1 | 0.48 | 5.79 | 0.08 | 17.2 | 90.3 | 99.8 |

(*1) IPC: isophthaloyl chloride,
(*2) TMC: trimesoyl chloride

EXAMPLE 2

A composite membrane was prepared in the same way as in Example 1, and then heat-treated in a hot air dryer at 115° to 120° C. for 10 minutes. The membrane showed a water flux of 68 liters/m$^2$.hr, a salt rejection of 16.5%, and a sucrose rejection of 97.3%. Since the polymer used did not have self-gelling ability, only the crosslinked layer was separated as shown in Referential Example 3. The crosslinked layer had a cation exchange capacity of 1.34 meq./g-dried crosslinked layer, an anion exchange capacity of 3.92 meq./g-dried crosslinked layer, and an ion exchange capacity ratio of 0.34.

EXAMPLES 3 TO 8

Example 1 was repeated except that the amount of 1 N hydrochloric acid and the type and concentration of the crosslinking agent were changed as shown in Table 2. The properties of the resulting composite membranes are also shown in Table 2.

TABLE 2

| Example | Amount of 1N HCl added (ml) | Crosslinking agent Type | Amount (%) | Cation exchange capacity (meq./g) | Anion exchange capacity (meq./g) | Ion exchange capacity (meq./g) | Water flux (liters/m$^2$.hr) | NaCl rejection (%) | Sucrose rejection (%) |
|---|---|---|---|---|---|---|---|---|---|
| 3 | 28 | SPC (*3) | 0.5 | 2.72 | 3.38 | 0.81 | 45 | 17.2 | 90.2 |
| 4 | 0 | TMC | 6.0 | 0.83 | 4.87 | 0.17 | 37 | 18.5 | 97.2 |
| 5 | 14 | PMC (*4) | 1.0 | 1.20 | 2.89 | 0.42 | 63 | 14.7 | 86.5 |
| 6 | 14 | TMC | 2.0 | 1.60 | 4.03 | 0.40 | 54 | 24.5 | 98.1 |
| 7 | 7 | TMC | 2.0 | 1.34 | 4.80 | 0.28 | 49 | 28.3 | 99.1 |
| 8 | 28 | TMC | 1.0 | 1.26 | 3.78 | 0.33 | 53 | 21.3 | 94.8 |

(*3) SPC is a compound of the following formula

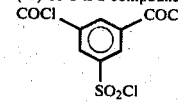

(*4) PMC is a compound of the following formula

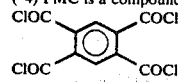

EXAMPLE 9

20 g of a 25% aqueous solution of polydiallylamine hydrochloride (a product of Nitto Spinning Co., Ltd.; intrinsic viscosity 0.44, ammonium salt equivalent 8.3 meq./g) was added to 459 ml of water, and with stirring, 208 ml of a 1 N aqueous solution of sodium hydroxide was added. A composite membrane was prepared in the same way as in Example 1 using the resulting solution. The composite membrane showed a water flux of 78 liters/m².hr, a salt rejection of 11.2%, a sucrose rejection of 94.3%. The crosslinked layer of this membrane had a cation exchange capacity of 0.28 meq./g, an anion exchange capacity of 1.59 meq./g and an ion exchange capacity ratio of 0.18.

COMPARATIVE EXAMPLE 3

A composite membrane was prepared in the same way as in Example 9 except that the amount of water added was changed to 451 ml and the amount of the 1 N aqueous sodium hydroxide solution was changed to 29.1 ml. The resulting composite membrane showed a water flux of 12.3 liters/m².hr, a salt rejection of 75.4%, a sucrose rejection of 99.5%, a cation exchange capacity of 0.04 meq./g, an anion exchange capacity of 2.72 meq./g, and an ion exchange capacity ratio of 0.015.

COMPARATIVE EXAMPLE 4

A composite membrane was prepared in the same way as in Example 9 except that 1.0% of tolylene 2,4-diisocyanate was used as the crosslinking agent. The resulting composite membrane showed a water flux of 7.4 liters/m².hr, a salt rejection of 96.2%, a sucrose rejection of 99.9%, a cation exchange capacity of 0 meq./g, and an anion exchange capacity of 1.87 meq./g.

EXAMPLES 10 TO 16

Composite membranes were prepared in the same way as in Example 9 except that the amount of the 1 N aqueous sodium hydroxide solution and the concentration and type of the crosslinking agent were changed as shown in Table 3. The properties of the resulting membranes are also shown in Table 3.

mole) of diallylamine hydrochloride, 16.3 g (0.10 mole) of dimethyldiallyl ammonium chloride and 4.2 g of ammonium persulfate, and the inside of the flask was purged with nitrogen. The system was then stirred for 5 hours at room temperature.

The resulting viscous reaction mixture was gradually added to a large amount of acetone to precipitate a white flaky polymer. The polymer was subjected thrice to a procedure of washing it with acetone and then filtering it, and then dried to afford 36.4 g of a polymer.

The polymer had an intrinsic viscosity, measured in a 1/10 N NaCl aqueous solution at 30° C., of 1.03.

The polymer was identified as a polymer having the following structural formula.

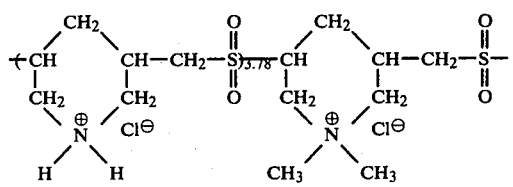

The resulting polymer (5 g) was dissolved in 300 ml of water, and 25 ml of a 1 N aqueous solution of sodium hydroxide was added. Furthermore, 2.5 g of piperazine was added to form a uniform aqueous solution. Using this solution, a composite membrane was prepared in the same way as in Example 1 except that a 1% by weight solvent (methyl ethyl ketone/n-hexane=15/85 by weight) solution of 5-sulfoisophthaloyl chloride was used as the crosslinking agent. The resulting composite membrane showed a water flux of 75 liters/m².hr, an NaCl rejection of 16.7% and a sucrose rejection of 96.2%. The crosslinked layer had a cation exchange capacity of 1.10 meq./g, an anion exchange capacity of 3.05 meq./g and an ion exchange capacity ratio of 0.36.

TABLE 3

| Example | Amount of 1N NaOH | Crosslinking agent (%) | Cation exchange capacity (meq./g) | Anion exchange capacity (meq./g) | Ion capacity exchange ratio | Water flux (liters/m².hr) | NaCl rejection (%) | Sucrose rejection (%) |
|---|---|---|---|---|---|---|---|---|
| 10 | 20.8 | IPC (1.0) | 0.25 | 2.35 | 0.11 | 82 | 16.5 | 90.7 |
| 11 | 20.8 | SPC (1.0) | 0.79 | 2.16 | 0.37 | 67 | 13.8 | 87.5 |
| 12 | 20.8 | TMC (4.0) | 1.02 | 2.43 | 0.42 | 73 | 14.3 | 89.7 |
| 13 | 10.4 | TMC (2.0) | 0.89 | 2.87 | 0.31 | 88 | 17.3 | 98.5 |
| 14 | 10.4 | IPC (2.0) | 0.28 | 2.65 | 0.11 | 52 | 18.4 | 88.3 |
| 15 | 5.2 | TMC (1.0) | 1.04 | 3.43 | 0.30 | 76 | 15.3 | 91.3 |
| 16 | 20.8 | IPC/TMC (=½) (1.0) | 0.68 | 2.68 | 0.25 | 57 | 18.4 | 94.7 |

EXAMPLE 17

Dehydrated and distilled dimethyl sulfoxide (300 ml) was put into a 500 ml four-necked flask equipped with a stirrer, a thermometer and a reflux condenser, and 32 g (0.50 mole) of dry sulfur dioxide gas was blown into it. Subsequently, the flask was charged with 53.4 g (0.40

EXAMPLES 18 AND 19

Composite membranes were prepared in the same way as in Example 17 except that the crosslinking agents shown in Table 4 were obtained. The properties of the resulting composite membranes are shown in Table 4.

TABLE 4

| Example | Crosslinking agent (%) | Cation exchange capacity (meq./g) | Anion exchange capacity (meq./g) | Ion exchange capacity ratio | Water flux liters/m²hr | NaCl rejection (%) | Sucrose rejection (%) |
|---|---|---|---|---|---|---|---|
| 18 | SPC (1.0) | 1.08 | 2.41 | 0.45 | 54 | 18.2 | 97.3 |

TABLE 4-continued

| Example | Crosslinking agent (%) | Cation exchange capacity (meq./g) | Anion exchange capacity (meq./g) | Ion exchange capacity ratio | Water flux liters/ m²hr | NaCl rejection (%) | Sucrose rejection (%) |
|---|---|---|---|---|---|---|---|
| 19 | TOMC (*5) (1.0) | 1.15 | 2.67 | 0.43 | 62 | 12.3 | 93.4 |

(*5) TOMC is a compound of the following formula

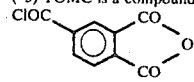

EXAMPLES 20 TO 24

The polymers shown in Table 5 were prepared in the same way as in Example 17 except that the ratio between diallylamine hydrochloride and dimethyl diallyl ammonium chloride was changed. Using the resulting polymers, composite membranes were prepared in the same way as in Example 17 except that the crosslinking agents shown in Table 5 were used.

TABLE 5

| Example | Polymer | Intrinsic viscosity | Crosslinking agent (%) | Cation exchange capacity (meq./g) | Anion exchange capacity (meq./g) | Ion exchange capacity (meq./g) | Water flux (liters/m²hr) | NaCl rejection (%) | Sucrose rejection (%) |
|---|---|---|---|---|---|---|---|---|---|
| 20 | | 0.28 | TMC (2.0) | 0.81 | 2.78 | 0.29 | 67 | 16.3 | 98.2 |
| 21 | | | IPC (1.0) | 0.26 | 3.02 | 0.09 | 28 | 17.2 | 86.7 |
| 22 | | | SPC (1.0) | 1.23 | 3.09 | 0.40 | 54 | 16.3 | 88.2 |
| 23 | | 0.36 | TMC (1.0) | 2.41 | 3.41 | 0.71 | 42 | 14.8 | 92.8 |
| 24 | | | SPC (1.0) | 1.78 | 3.28 | 0.54 | 78 | 16.3 | 94.2 |

EXAMPLE 25

Thirty grams of a 30% aqueous solution of polyethyleneimine (molecular weight 70,000; a product of Nippon Shokubai Kagaku Kogyo Co., Ltd.) was dissolved in 100 ml of ethanol, and reacted with 10.4 g of ethyl iodide at 50° to 60° C. for 5 hours. The ethanol and the unreacted ethyl iodide were removed by distillation to afford ethylated polyethyleneimine having an ammonium salt equivalent of 3.42 meq./g-dried polymer and a total primary and secondary amine equivalent of 4.52 meq./g-dried polymer. Using the resulting polymer, a composite membrane was prepared in the same way as in Example 1. The resulting composite membrane had a water flux of 72 liters/m²·hr, an NaCl rejection of 18.4% and a sucrose rejection of 98.2%. The crosslinked layer of this membrane showed a cation exchange capacity of 0.52 meq./g-dried crosslinked layer, an anion exchange capacity of 2.02 meq./g-dried crosslinked layer and an ion exchange capacity ratio of 0.22.

EXAMPLES 26 TO 28

Example 25 was repeated except that the amount of ethyl iodide and the type and concentration of the crosslinking agent were changed as shown in Table 6. The properties of the resulting composite membranes are shown in Table 6.

TABLE 6

| Example | Amount of ethyl iodide (g) | Crosslinking agent (%) | Cation exchange capacity (meq/g) | Anion exchange capacity (meq/g) | Ion exchange capacity ratio | Water flux (liters/ m²·hr) | NaCl rejection (%) | Sucrose rejection (%) |
|---|---|---|---|---|---|---|---|---|
| 26 | 10.4 | SPC (2.0) | 2.72 | 3.38 | 0.81 | 45 | 27.3 | 92.1 |
| 27 | 6.5 | TMC (4.0) | 1.02 | 3.42 | 0.30 | 64 | 21.4 | 95.3 |
| 28 | 16.0 | TMC (1.0) | 0.87 | 4.53 | 0.19 | 53 | 19.3 | 97.3 |

EXAMPLE 29

A three-necked flask equipped with a stirrer, a thermometer and a dropping funnel was charged with 80 g of distilled water and 21.9 g of triethylene tetramine (a product of Tokyo Kasei Kogyo Kabushiki Kaisha; with an amino equivalent of 27.2 meq/g), and they were mixed to form a solution. To the solution was added 7.4 g (0.025 mole) of triglycidyl isocyanurate ("ARALDITE" TGIC, a product of Nagase Sangyo Kabushiki Kaisha; with an epoxy equivlent of 105 g/eq.), and the mixture was stirred. The mixture was then heated to 50° C., and stirred for about 3 hours until it became a uniform solution. With stirring at the same temperature, 2.4 g (0.0125 mole) of bisphenol A diglycidyl ether ("EPI-KOTE" 828, a product of Shell Chemical Co.; with an epoxy equivalent of 184 to 194) was added through the dropping funnel over the course of 30 minutes. The mixture was further stirred for 3 hours at the same temperature, and allowed to cool to room temperature, followed by standing for about 20 hours.

The resulting reaction mixture was filtered through a microfilter, and the filtrate was diluted with distilled water until the concentration of the polyaddition product became 2.5% by weight. The resulting polyaddition product had a hydroxyl equivalent of 2.4 meq/g and an amino equivalent of 12.4 meq/g.

To 500 g of the resulting solution was added 27 ml of 1 N hydrochloric acid, and using the resulting solution, a composite membrane was prepared in the same way as in Example 1. The resulting composite membrane was tested for performance in reverse osmosis. It was found to have a water flux of 42 liters/m$^2$.hr, a salt rejection of 25.7%, and a sucrose rejection of 98.2%. The crosslinked layer of this membrane showed a cation exchange capacity of 1.32 meq/g-dried polymer, an anion exchange capacity of 2.16 meq/g-dried crosslinking layer, and an ion exchange capacity ratio of 0.61.

EXAMPLE 30

A solution of 10 g of poly(3,5-dichloromethyloxacyclobutane) (Penton, a registered trademark for a product of Hercules Inc.) having a number average molecular weight of 20,000 in 100 ml of N-methylpyrrolidone was added to 130 g of ethylenediamine and reacted at 100° C. for 20 hours. The reaction mixture was then poured into 1 liter of tetrahydrofuran, and washed several times with tetrahydrofuran to afford a polyamino polymer having the following structure and an intrinsic viscosity, determined in a 1/10 N aqueous NaCl at 30° C., of 0.12.

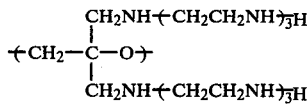

When a 50% by weight aqueous solution of this polymer was heat-treated by the method of Referential Example 4, it showed a self-gelling ratio of 45.1%.

Five grams of this polymer was dissolved in 500 ml of distilled water, and 13 ml of 1 N hydrochloric acid was added. A composite membrane was prepared from this solution by the same method as in Example 1. The resulting composite membrane had a water flux of 51 liters/m$^2$.hr, an NaCl rejection of 17.2% and a sucrose rejection of 93.4%. The crosslinked layer of this membrane showed a cation exchange capacity of 0.66 meq./g-dried crosslinked layer, an anion exchange capacity of 1.65 meq./g-dried crosslinked layer and an ion exchange capacity ratio of 0.40.

EXAMPLE 31

Distilled sulfonyl chloride (150 ml) was put into a 500 ml. three-necked flask equipped with a dropping funnel and a reflux condenser, and while stirring the material, 20 g of polymethacrylic acid (a number average molecular weight 100,000) was added dropwise from the dropping funnel over the course of 2 hours. After the addition, the temperature of the inside of the flask was raised to 50°–60° C., and the mixture was stirred further for 3 hours. Thus, the reaction mixture became a uniform solution. Removal of the sulfonyl chloride by distillation afforded poly(methacryloyl chloride) as a reddish brown solid. A 200 ml flask was charged with 100 ml of distilled water and 8.6 g of piperazine, and after completely dissolving the piperazine by stirring, 4.4 g of the resulting poly(methacryloyl chloride) was added, and the mixture was stirred at room temperature for 1 hour. The resulting aqueous solution of piperazine-modified poly(methacryloyl chloride) was filtered, and 50 ml of diethyl ether was added to precipitate and piperazine-modified polymer. The amine equivalent of the polymer was 4.9 milliequivalents/g.

Five grams of the polymer was dissolved in 500 ml of distilled water, and 7 ml of 1 N hydrochloric acid was added. A composite membrane was prepared in the same way as in Example 1 using the aqueous solution. The composite membrane was subjected to the reverse osmosis test, and found to have initial properties represented by a water flux of 84 liters/m$^2$.hr and a salt rejection of 15.1% and a sucrose rejection of 87.4%. The crosslinked layer of this membrane showed a cation exchange capacity of 0.46 meq./g-dried crosslinked layer, an anion exchange capacity of 0.96 meq./g-dried crosslinked layer and an ion exchange capacity ratio of 0.48.

EXAMPLE 32

A 500 ml. three-necked round-bottomed flask equipped with a stirrer, a thermometer and a reflux condenser was charged with 80 ml of dried and distilled benzene, 8.6 g of maleic anhydride recrystallized from chloroform, 8.6 g of distilled methyl acrylate and 0.7 g of azobisisobutyronitrile (AIBN). After purging the inside of the flask with nitrogen, the temperature of the inside of the flask was raised to 70° C., and the mixture was stirred for 8 hours, when a viscous polymer precipitated. The resulting polymer was thoroughly washed with anhydrous benzene, and dried at 50° C. under reduced pressure to afford 11.3 g of a white viscous solid polymer which was determined to be a 1:1 block copolymer of methyl acrylate and maleic anhydride as a result of IR and NMR analyses.

A 200 ml. flask was charged with 14.6 g of triethylene-tetramine [H$_2$N$-$(CH$_2$CH$_2$NH$)-_3$H], 150 ml of distilled water and 8.6 g of the resulting copolymer. The inside of the flask was purged with nitrogen, and heated to 50° C. When the mixture was stirred for 3 hours, the above polymer became completely water-soluble. Addition of 100 ml of diethyl ether to an aqueous solution of the amine-modified polymer resulted in precipitation of the polymer. The polymer was dried under reduced pressure at 50° C. to afford 16.2 g of a viscous faintly yellow solid polymer. The amine equivalent of the polymer was determined by the peracetic acid-glacial acetic acid titration method, and found to be 10.3 milliequivalents/g.

The modified polymer obtained was dissolved in distilled water, and filtered on a microfilter to form a 1% by weight aqueous solution.

A composite membrane was prepared in the same way as in Example 1 using this solution. The composite membrane had a water flux of 54 liters/m$^2$.hr, an NaCl rejection of 17.3%, and a sucrose rejection of 85.7%. The crosslinked layer showed a cation exchange capacity of 1.12 meq./g-dried crosslinked layer, an anion exchange capacity of 0.81 meq./g-dried crosslinked layer, and an ion exchange capacity ratio of 1.38.

EXAMPLE 33

A polymer was prepared in the same way as in Example 32 except that 10.7 g of 2-chloroethyl vinyl ether was used instead of the methyl acrylate in Example 32. The total amine equivalent of this polymer was 12.3 meq./g. 10 grams of the polymer was dissolved in 500 ml of distilled water, and 20 ml of 1 N hydrochloric acid was added. And a composite membrane was prepared in the same way as in Example 32. The resulting composite membrane had a water flux of 83 liters/m$^2$.hr, an NaCl rejection 14.2% and a sucrose rejection of 92.5%. The crosslinked layer showed a cation exchange capacity of 0.90 meq./g-dried crosslinked polymer, an anion exchange capacity of 0.71 meg./g-dried crosslinked polymer, and an ion exchange capacity ratio of 1.30.

EXAMPLE 34

Ten grams of polymethyl acrylate (molecular weight about 100,000) was dissolved in 95 g of N-methylpyrrolidone, and 120 g of diethylenetriamine was added. The mixture was heated at 120° C. for 10 hours.

The mixture was put into 1 liter of tetrahydrofuran to precipitate the reaction product which was washed several times with tetrahydrofuran to form a amino polymer of the following structure.

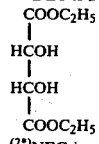

The polymer had an intrinsic viscosity, measured in 1/10 N aqueous NaCl, of 0.95. When a 50% solution of this polymer was heat-treated at 120° C. for 30 minutes in the same way as in Referential Example 4, its self-gelling ratio was 43%.

Four grams of this polymer was dissolved in 500 ml of distilled water, and 8 ml of 1 N hydrochloric acid was added. A composite membrane was prepared in the same way as in Example 1 using the resulting solution. The resulting composite membrane had a water flux of 83 liters/m$^2$.hr, an NaCl rejection of 22.0% and a sucrose rejection of 94.5%. The crosslinked layer had a cation exchange capacity of 0.83 meq./g-dried crosslinked layer, an anion exchange capacity of 1.48 meq./g-dried crosslinked layer and an ion exchange capacity ratio of 0.58.

EXAMPLES 35 TO 38

Each of the internal crosslinking agents shown in Table 7 was added to polyethylenimine partially neutralized with hydrochloric acid in the same way as in Example 1. Using the resulting amino polymer solution, a composite membrane was prepared in the same way as in Example 1. The ion exchange capacities of the resulting composite membranes are shown in Table 7.

The resulting membranes were each heat-treated at 110° C. for 10 minutes, and the properties of the heat-treated composite membranes were measured. The results are also shown in Table 7.

TABLE 7

| | | Membrane before heat-treating | | | Heat-treated membrane | | |
|---|---|---|---|---|---|---|---|
| Example | Internal crosslinking agent (%) | Cation exchange capacity (meq./g) | Anion exchange capacity (meq./g) | Ion exchange capacity ratio | Water flux (liters/ m$^2$hr) | NaCl rejection (%) | Sucrose rejection (%) |
| 35 | (*1)DET (0.2) | 1.19 | 3.22 | 0.33 | 68.4 | 19.2 | 98.9 |
| 36 | DET (0.4) | 1.04 | 3.62 | 0.29 | 62.7 | 23.3 | 99.2 |
| 37 | (2*)NEG (0.6) | 0.94 | 2.89 | 0.32 | 45.6 | 17.5 | 96.7 |
| 38 | (3*)Ep828 (0.4) | 0.87 | 3.04 | 0.29 | 43.8 | 15.2 | 96.5 |

(1*)DET is a compound of the following formula

COOC$_2$H$_5$
|
HCOH
|
HCOH
|
COOC$_2$H$_5$ (2*)NEG is a compound of the following formula

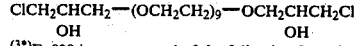

ClCH$_2$CHCH$_2$—(OCH$_2$CH$_2$)$_9$—OCH$_2$CHCH$_2$Cl
   OH                                    OH (3*)Ep828 is a compound of the following formula

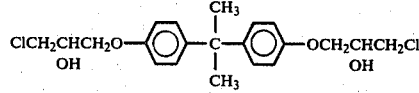

EXAMPLES 39 AND 40

A composite membrane was prepared in the same way as in Example 29 except that 1 N hydrochloric acid was not added, and separately, each of the internal crosslinking agents shown in Table 8 was added. The ion exchange capacities of the resulting composite membrane are shown in Table 8.

The composite membrane was heat-treated at 110° C. for 10 minutes. The properties of the heat-treated composite membrane are shown in Table 8.

TABLE 8

| Example | Internal crosslinking agent (%) | Cation exchange capacity (meq./g) | Anion exchange capacity (meq./g) | Ion exchange capacity ratio | Water flux (liters/ m$^2$hr) | NaCl rejection (%) | Sucrose rejection (%) |
|---|---|---|---|---|---|---|---|
| 39 | NEG (0.45) | 0.43 | 2.04 | 0.21 | 47.8 | 14.7 | 96.5 |

TABLE 8-continued

| Example | Internal crosslinking agent (%) | Cation exchange capacity (meq./g) | Anion exchange capacity (meq./g) | Ion exchange capacity ratio | Water flux (liters/m²hr) | NaCl rejection (%) | Sucrose rejection (%) |
|---|---|---|---|---|---|---|---|
| 40 | Ep828 (0.4) | 0.72 | 2.72 | 0.26 | 38.9 | 26.3 | 99.0 |

What we claim is:

1. An amphoteric ion-permeable composite membrane having an NaCl and a sucrose rejection having the relation defined by the following equation:

$$2\times(\text{sucrose rejection in \%}) - (\text{NaCl rejection in \%}) \geq 150$$

and an NaCl rejection of at most 40% and a sucrose rejection of at least 80%, said member composed of a microporous substrate, and supported on the substrate, a thin amphoteric ion-exchange film formed of an active amino group-containing polymer which has been interfacially crosslinked at least at the surface portion of the thin film, said membrane being produced by forming a thin layer comprising an active amino group-containing polymer containing 1.0 to 23 milliequivalents/g, as an amino equivalent, of an active amino group selected from primary and secondary amino groups and 0 to 18 milliequivalents/g, as an amino equivalent, of a tertiary amino group and/or an ammonium salt group per molecule with the total amino content thereof being in the range of 2.0 to 23 milliequivalents/g on the microporous substrate and then contacting the thin layer on the substrate interfacially with a polyfunctional aromatic compound to interfacially crosslink the thin layer, said polyfunction aromatic compound containing at least two functional groups selected from carbonyl halide groups, sulfonyl halide groups, carboxylic acid anhydride groups, sulfonic acid anhydride groups and derivative groups of carboxylic acids and sulfonic acids having equivalent reactivity to the aforesaid halide and anhydride groups; the interfacially crosslinked polymer zone of the thin film containing at least one structural unit of the formula

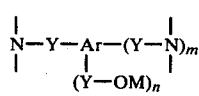

(I)

wherein Ar represents an aromatic ring, Y represents CO or SO₂ provided that (m+n+1) group Y bonded to the group Ar are identical or different, M represents an atom or atomic grouping capable of being split off as a cation, and m and n each represent an integer of 0 or more provided that m+n=1-3, said polymer zone further containing a structural unit of formula (I) in which m is not zero when it contains a structural unit of formula (I) in which m is zero, and further containing a structural unit of formula (I) in which n is not zero when it contains a structural unit of formula (I) in which n is zero, and additionally containing at least 0.5 milliequivalents/g, based on the dry crosslinked polymer, of an ammonium salt group as an anion-exchange group and at least 0.05 milliequivalents/g of the dry crosslinked polymer of the group -YOM in formula (I) as a cation-exchange group, the equivalent ratio of the ammonium salt group to the group -YOM being in the range of from 20:1 to 1:2.

2. The composition membrane of claim 1 which has an NaCl and a sucrose rejection having the relation defined by the following equation:

$$2\times(\text{sucrose rejection in \%}) - (\text{NaCl rejection in \%}) \geq 160$$

3. The composite membrane of claim 1 which has an NaCl rejection of at most 30% and a sucrose rejection of at least 85%.

4. The composite membrane of claim 1 wherein Ar in formula (I) represents a benzene ring.

5. The composite membrane of claim 1 wherein the interfacially crosslinked polymer zone contains 0.5 to 8.0 milliequivalents, per gram of the interfacially crosslinked polymer (dry), of ammonium salt groups and 0.05 to 5.0 milliequivalents, per gram of the interfacially crosslinked polymer (dry), of the group -YOM in formula (I).

6. The composite membrane of claim 1 wherein the equivalent ratio of the ammonium salt groups to the group -YOM is in the range of from 15:1 to 2:3.

7. The composite membrane of claim 1 wherein the equivalent ratio of the ammonium salt groups to the group -YOM is in the range of from 10:1 to 1:1.

8. The composite membrane of claim 1 wherein the active amino group-containing polymer contains 2.0 to 20 milliequivalents/g, as amino equivalent, of an active amino group selected from primary and secondary amino groups and 1 to 12 milliequivalents/g, as amino equivalent, of a tertiary amino group and/or an ammonium salt group with the total amino content being in the range of 3.0 to 23 milliequivalents/g.

9. The composite membrane of claim 8 wherein the total amino content is in the range of 5.0 to 23 milliequivalents/g.

10. The composite membrane of claim 1 wherein the active amino group-containing polymer has a number average molecular weight of about 500 to about 200,000.

11. The composite membrane of claim 1 wherein the active amino group-containing polymer has a solubility at 20° C. of not less than 5% by weight in water or a water-miscible solvent having a boiling point of not more than 140° C. and selected from alcohols, ethers and ketones.

12. The composite membrane of claim 1 wherein the active amino group-containing polymer is an aliphatic active amino group-containing polymer.

13. The composite membrane of claim 12 wherein the number of carbon atoms which constitute the chain connecting two adjacent amino groups in the same molecule is mainly from 2 to 6.

14. The composite membrane of claim 1 wherein the active amino group-containing polymer is capable of gelling by itself upon heating.

15. The composite membrane of claim 1 wherein the polyfunctional aromatic compound has 2 or 3 functional groups.

16. The composite membrane of claim 1 wherein the polyfunctional aromatic compound is trifunctional aromatic compound, or a mixture of a difunctional aromatic compound and a trifunctional aromatic compound.

17. The composite membrane of claim 16 wherein the di- or or tri-functional compound is isophthaloyl chloride, terephthaloyl chloride, trimesoyl chloride or 5-chlorosulfonylisophthaloyl chloride.

18. The composite membrane of claim 1 wherein the active amino group-containing polymer is substantially free from both a tertiary amino group and an ammonium salt group, and is contacted with a solution containing the polyfunctional aromatic compound in a concentration of 2 to 10% by weight.

19. The composite membrane of claim 1 wherein the active amino group-containing polymer substantially contains a tertiary amino group and/or an ammonium salt group, and is contacted with a solution containing the polyfunctional aromatic compound in a concentration of 0.2 to 4.0% by weight.

20. The composite membrane of claim 1 wherein the thin film has a thickness of 500 to 20,000 Å.

21. The composite membrane of claim 1 wherein the microporous substrate is a polysulfone substrate.

22. An amphoteric ion-permeable composite membrane having improved stability, prepared by heat-treating the composite membrane of any one of claims 1 to 21.

23. The composite membrane of claim 22 wherein the heat-treatment is carried out at a temperature of at least 70° C. for a period of at least 1 minute.

24. The composite membrane of claim 22 which is prepared by heat-treating the composite membrane of claim 1 wherein the active amino group-containing polymer is capable of gelling by itself upon heating.

25. The composite membrane of claim 22 which is prepared by heat-treating the composite membrane of claim 1 wherein the thin layer further contains an internal cross-linking agent having at least two functional groups substantially incapable of reacting with either the primary or secondary amino group in the active amino group-containing polymer at the temperature at which the interfacial crosslinking is carried out, but capable of easily reacting with the primary or secondary amino group or both in the polymer at a temperature at least 30° C. higher than the crosslinking temperature.

* * * * *